US012806532B2

(12) United States Patent
Lomax

(10) Patent No.: US 12,806,532 B2

(45) **Date of Patent: *Nov. 24, 2026**

(54) VIDEO GAMING HEALTH ENHANCER

(71) Applicant: Zamar Lomax, San Diego, CA (US)

(72) Inventor: Zamar Lomax, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/899,740

(22) Filed: Sep. 27, 2024

(65) Prior Publication Data

US 2026/0108815 A1 Apr. 23, 2026

Related U.S. Application Data

(63) Continuation-in-part of application No. 18/396,654, filed on Dec. 26, 2023, now Pat. No. 12,151,160.

(51) Int. Cl.

| | |
|---|---|
| ***G16H 40/67*** | (2018.01) |
| ***A63F 13/79*** | (2014.01) |
| ***G16H 50/50*** | (2018.01) |

(52) U.S. Cl.

CPC ............ *A63F 13/79* (2014.09); *G16H 40/67* (2018.01); *G16H 50/50* (2018.01)

(58) Field of Classification Search

CPC ......... A63F 13/79; G06H 40/67; G06H 50/50

See application file for complete search history.

(56) References Cited

U.S. PATENT DOCUMENTS

| | | | |
|---|---|---|---|
| 5,001,632 | A | 3/1991 | Hall-Tipping |
| 5,362,069 | A | 11/1994 | Hall-Tipping |
| 8,298,078 | B2 | 10/2012 | Sutton |
| 8,308,562 | B2 | 11/2012 | Patton |
| 9,498,705 | B2 | 11/2016 | Cronin et al. |
| 9,511,289 | B2 | 12/2016 | Bond et al. |
| 10,394,324 | B2 | 8/2019 | Drake et al. |
| 10,586,420 | B1 | 3/2020 | Bagherzadeh et al. |
| 11,130,064 | B2 | 9/2021 | Kahn, II et al. |
| 11,707,680 | B2 | 7/2023 | Bartolome et al. |
| 11,772,000 | B2 | 10/2023 | Barcias |
| 2007/0167689 | A1 | 7/2007 | Ramadas et al. |
| 2014/0121017 | A1 | 5/2014 | Mandryk et al. |
| 2024/0390788 | A1 | 11/2024 | Benbassat |
| 2024/0390798 | A1 | 11/2024 | Benbassat |
| 2024/0390806 | A1 | 11/2024 | Benbassat |
| 2024/0390807 | A1 | 11/2024 | Benbassat |

*Primary Examiner* — Thomas H Henry

(57) ABSTRACT

Systems and methods for a computer-based gaming system and/or its associated components to receive and analyze a user's vital sign(s) information and in response to a detected unhealthy condition, alter functionalities to a computer-based gaming system and its associated components in a manner to improve the unhealthy condition.

20 Claims, 15 Drawing Sheets

VIDEO GAMING HEALTH ENHANCER

CROSS-REFERENCE TO RELATED APPLICATIONS

This application is a continuation-in-part of and claims priority to U.S. patent application Ser. No. 18/396,654 filed Dec. 26, 2023, entitled "Video Gaming Health Enhancer." The entire content of the application is incorporated herein by reference.

TECHNICAL FIELD

This disclosure relates to video games and computer-based gaming systems, and, more particularly, to video gaming safety.

DESCRIPTION OF RELATED ART

Video and other types of computer-based gaming systems have been around for years. With the ongoing development of making video games more amusing and addictive, may bring problems. Video games may impose harmful stresses on players that can lead to deterioration in health.

Parental controls may be used to limit the amount of time a user is playing a video game; however, the results may not always be effective. Statistics reveal that a substantial 70% of gamers globally are aged 18 and older. This predominance of adult gamers raises a issue: traditional parental controls, predominantly designed for and implemented by parents for their children, may not be effective for this majority demographic.

In some cases, video games may issue warnings for their video games such as: health and safety warnings, age ratings and content warnings, stress and difficulty level warnings, online interaction warnings, motion sickness warnings, and extended play warnings. These warnings may not be effective because, due to the psychological effects an addictive and amusing video game may impose on a player, a player may simply ignore these warnings and proceed with their gaming sessions.

In some cases, health professionals may prescribe medications to players to help treat stress, anxiety and depression that may be brought upon by gaming sessions. However, this treatment may not always be safe and effective. These medications may not be effective on every player experiencing these symptoms. These medications may also bring on side effects to the player such as negatively impacting their cognitive and motor skills which may be crucial for a player to properly play and enjoy the video game which may cause more stress, depression, and anxiety on the player. There may be many more side effects of medications that negatively influence a player's health such as: weight gain, sleep disturbances, sexual dysfunction, mood swings, and increased anxiety or depression to name a few. Many players may not even seek or use such medications.

In some cases, a player may engage in non-pharmacological approaches to treat their condition(s) such as attending counseling or therapy sessions. However, this method may not always be effective. One issue may be financial and accessibility issues. Regular therapy sessions may be expensive and may not be covered by insurance. Additionally, access to qualified therapists, especially those specializing in gaming-related issues, may be limited in some areas. Another issue may be individual engagement and motivation. The effectiveness of therapy may largely depend on the individual's level of engagement and motivation. If a person is not fully committed to the process or is attending sessions due to external pressure (like family insistence), they may not benefit as much.

SUMMARY

A non-transitory computer-readable storage media may contain a program of instructions that may be run in conjunction with a computer-based gaming system that may generate digital media that a user of the gaming system may interact with in one or more ways. The computer-based gaming system may receive information indicative of at least one vital sign of the user. The computer-based gaming system may determine whether the received information is indicative of an unhealthy condition in the user that may be caused by one or more of the ways in which the user interacts with the digital media. In response to a determination that the received information is indicative of such an unhealthy condition in the user, the computer-based gaming system may alter one or more of the ways in which the user may interact with the digital media that is or are likely to be contributing to the unhealthy condition in the user in a manner that may improve the unhealthy condition. The computer-based gaming system may also or instead alter the environment surrounding the user to help relieve this unhealthy condition.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings illustrate examples. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Figure 1:
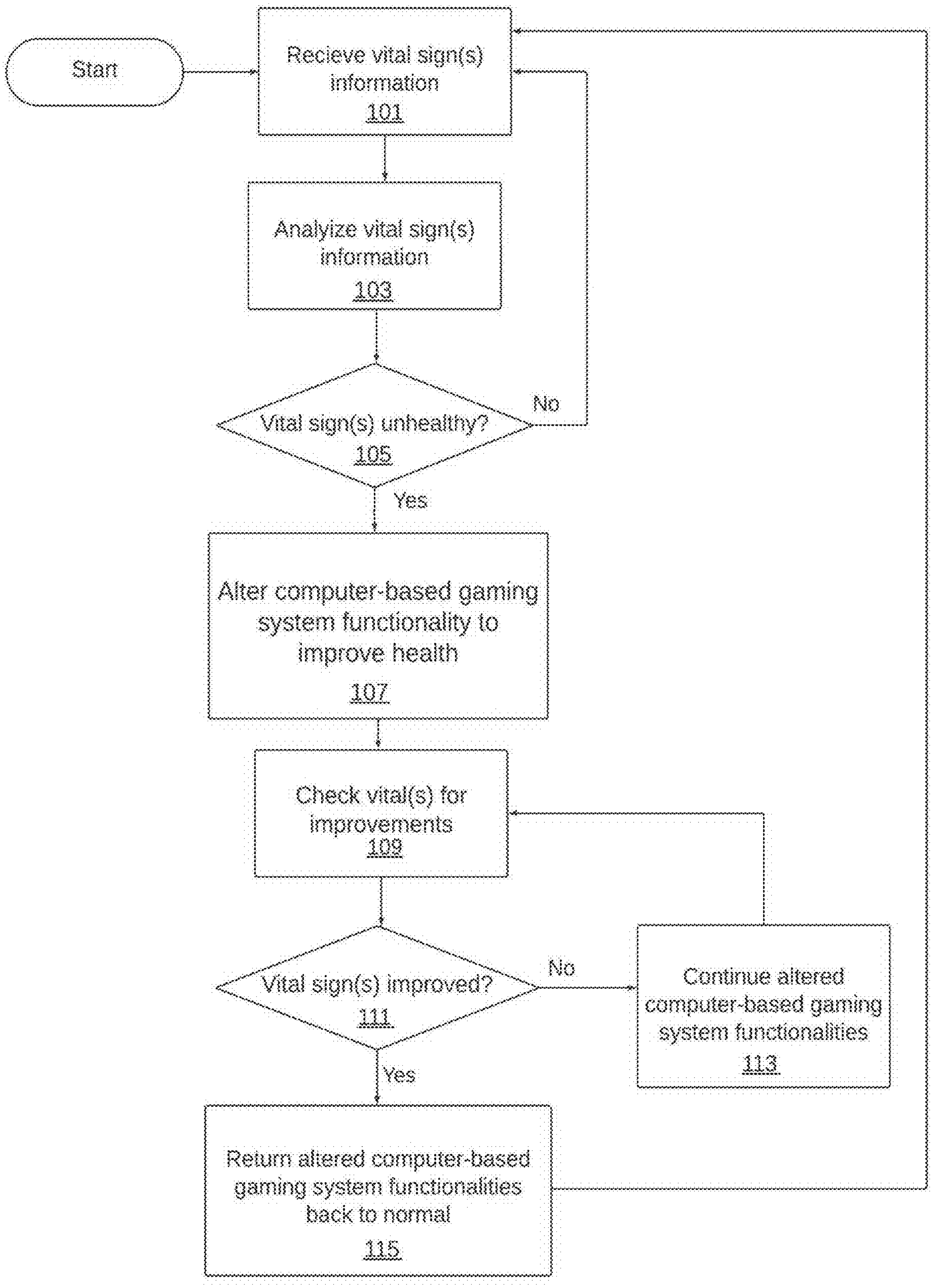
FIG. 1 is a flowchart of an example of a process of a computer-based gaming system.

FIG. 1 illustrates a process for enhancing user health during computer-based gaming system interaction. At step 101, the computer-based gaming system may receive vital sign(s) information. This information may be fundamental health metrics for assessing and monitoring a user's physiological, psychological, behavioral, and biometric status, essential for detecting potential unhealthy conditions.

At step 103, one or more vital sign detectors, integrated and/or attached and/or coupled with various devices and/or peripherals, may detect and/or analyze the vital signs. These devices may include, but are not limited to, input peripherals, wearable devices, digital media display devices, and components that are commonly used in conjunction with a computer-based gaming system.

Following data collection, the computer-based gaming system may analyze the vital sign(s) information to determine if the vital sign(s) indicate an unhealthy and/or potentially unhealthy condition as per step 105. The term 'unhealthy' may mean conditions that are harmful and/or potentially harmful, the user. The analysis may involve comparing the current vital sign(s) against predetermined and/or predefined health benchmarks and/or the user's historical and/or real-time health metrics. If the vital signs(s) are healthy, the computer-based gaming system loops back to "receive vital sign(s) information 101.

If unhealthy vital sign(s) are detected, the process may proceed to step 107, where the functionalities of the computer-based gaming system may be altered in a manner to improve the user's health.

Next process may reevaluate the user's vital signs at step 109.

Based on the reevaluation at step 111, if the user's vital signs have improved, the computer-based gaming system may return the altered functionalities to their original state as per step 115. If no improvement is observed, the computer-based gaming system may continue the altered functionalities as indicated at step 113.

Altering and/or alter and/or alteration and/or altered and/or alterable may mean, stopping, restricting, adding, reducing, lowering, increasing, activating, deactivating, blocking, removing, terminating, controlling, executing, modifying, assisting, displaying, replacing, changing, swapping, rotating, resolutions and processing, among others.

Altering and/or alter and/or alteration and/or altered may mean also mean at least one singular way in which the user interacts with the digital media such as altering the depiction of a single game element such as one spider, or more than one singular alteration but not all ways in which the user interacts with the digital media.

Timing of Alterations: Immediate alterations—Changes applied instantly upon detection of an unhealthy condition. Delayed alterations-Changes applied after a period of time and/or upon meeting certain conditions following the detection of an unhealthy condition.

Current Alterations—The computer-based gaming system may apply alterations to the user's current digital media interaction in response to a detected unhealthy condition.

Future Alterations—The computer-based gaming system may analyze upcoming digital media content and preemptively apply alterations. For example, If the computer-based gaming system detects that certain digital media element that appear on a video game virtual environment may contribute to a unhealthy condition and/or potentially unhealthy condition, the computer-based gaming system may scan future virtual environments or content for similar digital media elements and have these elements altered before the user encounters them. This may also be interpreted as preventing an unhealthy condition and/or potentially unhealthy condition from arising.

Past-Informed Alterations:—The computer-based gaming system may utilize historical data to inform alterations. For example, when a user revisits a saved game data or starts a new game on a video game they may have previously played, the computer-based gaming system may apply alterations based on previously vital sign information's and alterations from when the user previously played the game.

The computer-based gaming system may maintain a profile of effective alterations for each user, digital media content the user interacts with, or specific digital media elements.

These past-informed alterations may be automatically applied or suggested to the user when similar and/or the same gameplay scenarios are encountered.

After an alteration is made, the computer-based gaming system may wait a select period of time before making another alteration. The computer-based gaming system may wait for a select period of time to apply another alteration and/or to adjust one or more of the previously made alterations in a manner to improve the unhealthy condition of the user. The previously made alteration may last for a select period of time, and while this alteration is running, the standby phase may be initiated during any time period of the duration of the alteration, and the timing of this may determine when the next alteration is available to occur. The standby phase may also be initiated once the select time of the alteration is complete. The duration of the alteration may also last until the user's unhealthy condition improves or for a predetermined amount of time.

Figure 2:
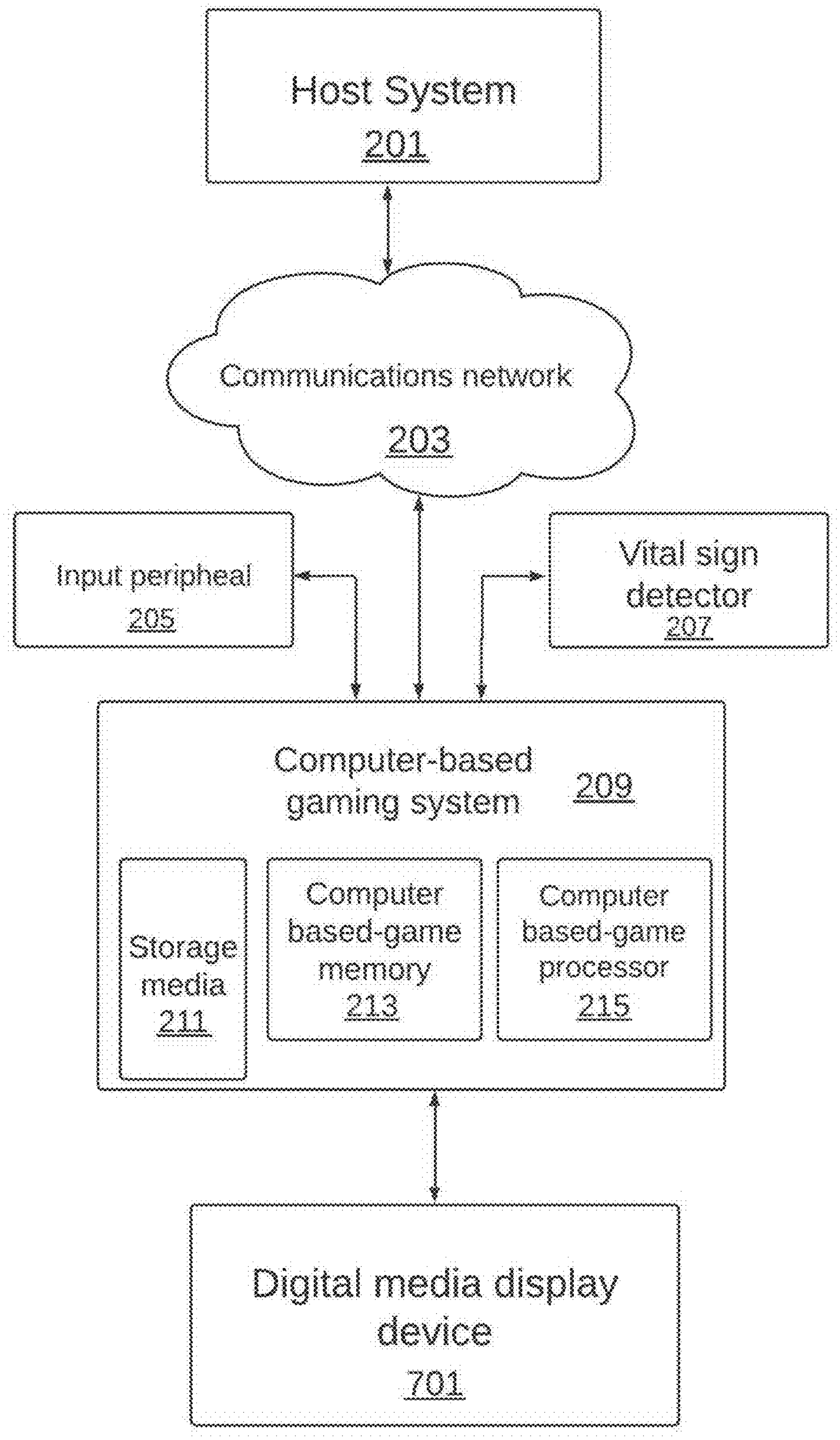
FIG. 2 is an example of a hardware topology diagram of a computer-based gaming system.

FIG. 2 illustrates a schematic detailing the architecture and interconnectivity inherent in a computer-based gaming system.

At the pinnacle of this architecture, the Host system 201 may function as the primary controller, facilitating communication and directing gaming operations. The Host system may take various forms, including but not limited to a server, a mainframe, a workstation, an embedded system, a gateway, cloud infrastructure, a virtual machine, a router, or an edge device. The processing and/or analysis and/or alteration of data may be conducted here.

The communications network 203 may function as a central hub for data exchange within the gaming system, leveraging a variety of networking technologies. These technologies may include, but are not limited to, Wi-Fi, Bluetooth, cellular networks, cloud services, fiber optic connections, Ethernet, and other wired or wireless communication methods. This communications network 203 may facilitate interactions between various system modules and provide access to a range of online services, including game hosting, media streaming, and other interactive user services. The communications network 203 may also be capable of processing, analyzing, and potentially altering data as part of its operational framework.

The Input peripheral 205 may capture user input through devices such as joysticks, gamepads, keyboards, and touch screens, among others. The processing and/or analysis and/or alteration of vital sign information may be conducted here.

The Vital sign detector 207, which may be integrated into and/or function alongside the computer-based gaming system 209, can be positioned on or near the user to monitor various physiological and/or psychological and/or biometric and/or behavioral health metrics. This vital sign detector 207 may be equipped with an array of sensors, each designed to capture data related to vital signs. These sensors may be capable of monitoring weight, and/or vocal functions, and/or ocular health, and/or auditory functions, and/or cardiac activity, and/or respiratory rate, and/or blood pressure, and/or thermoregulation, and/or expressive behaviors, and/or neurological functions. The collected data from these sensors may undergo processing and/or analysis, which could lead to alterations in various components of the gaming system.

Additionally, a camera and/or camcorder, and/or webcam may aid in determining unhealthy conditions through the analysis of facial expressions and/or body language and/or eye tracking. These imaging devices are capable of capturing visual cues that can be indicative of health issues, such as changes in facial expression, posture, and other physical behaviors.

Additionally, one or more vital sign detectors 207, integrated and/or attached and/or coupled with various devices and/or peripherals, may detect and/or analyze the vital signs. These devices may include, but are not limited to, input peripherals, wearable devices, display devices, and components used in conjunction with a computer-based gaming system. Techniques employed by these detectors may involve optical sensing, electrical bio-impedance, ultrasonography, acoustic sensing, temperature sensing, electroencephalography readings (EEG readings), facial detection, and/or electrical neural monitoring, for capturing a broad spectrum of a user's health metrics.

Additionally, computer-based gaming system may work in conjunction with a microphone and/or headset that listens to the user's words and/or tone. This auditory input may allow for the assessment of potentially unhealthy and/or unhealthy conditions by analyzing vocal characteristics.

These sensors may be capable of monitoring various vital signs, utilizing established medical and health monitoring technologies and/or techniques appropriate for each vital sign.

The computer-based gaming system 209 may serve as the execution platform for games and may include components such as a motherboard, storage devices, memory, processors, input peripherals, and output devices. It may include functionalities such as web browsing, media playback, messaging, photo and video capture, sound recording and editing, payment processing, pedometer tracking, cellular communications, time display, and Global Positioning System (GPS) services and/or others. The computer-based gaming system 209 may also support multiplayer environments for both online and local play. The processing and/or analysis and/or alteration of data may be conducted here. A computer-based gaming system 209 may be a smartphone, a handheld video game console, a home video game console, an AR (augmented reality) headset, a VR (virtual reality) headset, an MR (mixed reality) headset, a PC (personal computer), smart glasses, etc.

The computer-based game processor 215, typically known as the CPU, may manage the computational demands of gameplay, graphics rendering, and game mechanics. The processing and/or analysis and/or alteration of data may be conducted here.

Storage media 211 may store game files, user profiles, downloadable content, updates, and other personalizing data. It may also contain programs responsible for altering the gaming system's functionality. The processing and/or analysis and/or alteration of data may be conducted here.

Finally, the Digital media display device 701 may render digital media content and/or gaming content to the user, potentially employing various display technologies and connecting to the gaming system via multiple interfacing options. The processing and/or analysis and/or alteration of data may be conducted here.

The computer-based gaming system 209 may be equipped with functionalities to support online multiplayer gaming. This includes the necessary hardware and software components to enable networked play, allowing users to connect and/or interact with other players across various digital platforms. The computer-based gaming system 209 architecture may incorporate servers, networking hardware, and/or optimized software protocols designed to facilitate online play.

In the schematic architecture of the computer-based gaming system, 209 communications network 203 and/or vital sign detection capabilities may be integrated to support online gameplay involving health monitoring. This may enable the computer-based gaming system 209 to connect with other players over a network, allowing for the real-time exchange and/or analysis of vital sign data during multiplayer sessions.

The communications network 203 may be configured to manage high-bandwidth data transfer, ensuring accurate and prompt communication of vital sign information from each player. The computer-based gaming system 209 may also include algorithms and/or processing units capable of analyzing these health metrics, contributing to a responsive and health-conscious multiplayer gaming experience.

The computer-based gaming system 209, encompassing its integrated and/or connected hardware, and/or firmware, and/or software components which may include input peripheral 205 and/or a host system, 201 and/or a vital sign detector, 207 and/or a communications network 203 may employ a range of established health metric analysis methods and/or industry-standard software tools, to process and/or interpret data across various vital signs. In addition to monitoring a user's vital signs, the computer-based gaming system 209 may also be equipped to measure muscle activity in the user's wrist or hand, which may be used for detecting and managing conditions like arthritis. These tools and methods may be specifically tailored to effectively analyze and manage data related to various health metrics.

The processes and functionalities depicted in the flow chart of FIG. 1 may be executed in conjunction with any of the components illustrated in FIG. 2.

Figure 3:
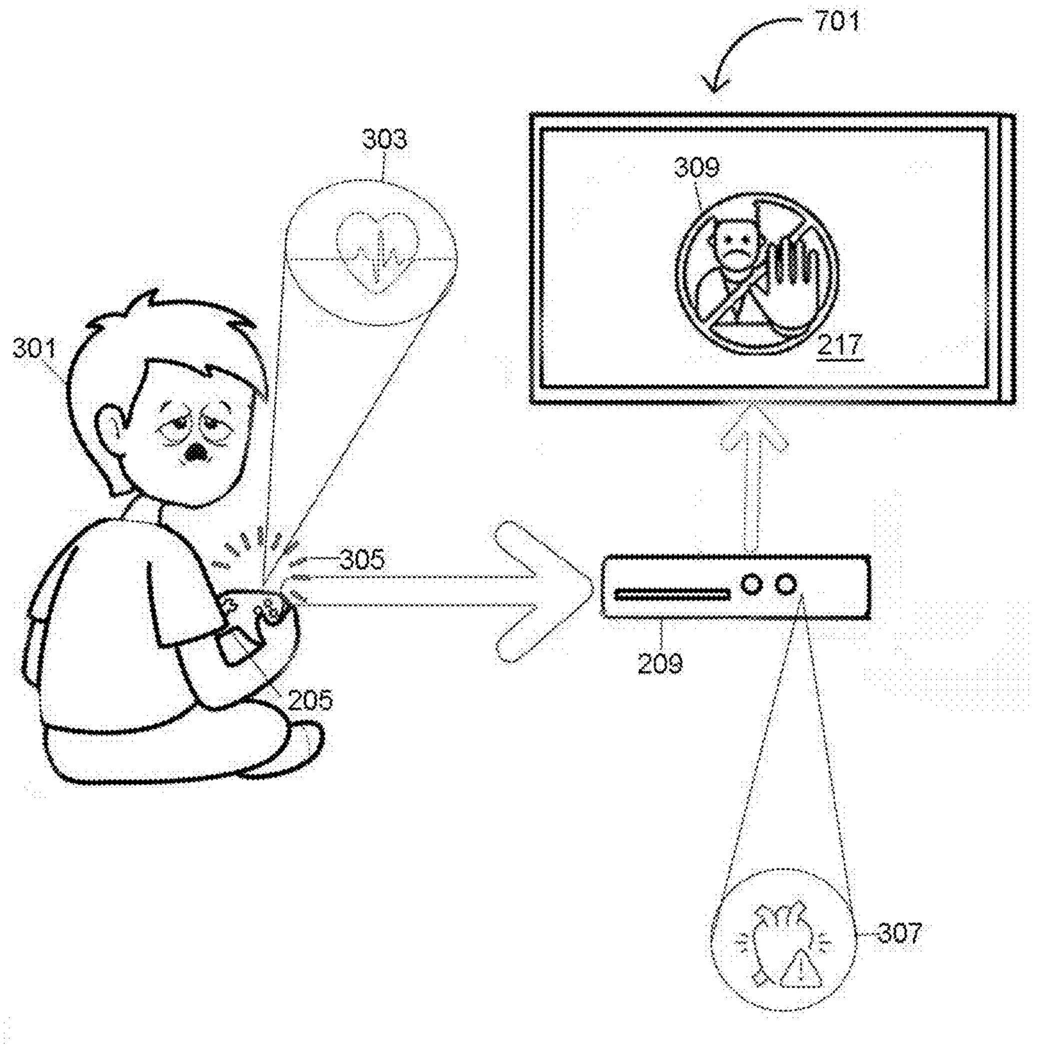
FIG. 3 is an example of a computer based-gaming system altering functionalities in the digital media response to a user's unhealthy condition.

FIG. 3 illustrates the response of a computer-based gaming system 209 when it detects an unhealthy condition 307 in a user 301. The user 301 is shown utilizing an input peripheral 205, which is capable of not only registering user inputs but also collecting vital sign information 305, such as heartbeat.

The input peripheral 205 is equipped with sensors that detect and transmit vital sign information 305 to the computer-based gaming system 209 for further analysis.

Upon determining indicators of an unhealthy condition 307 from the analysis, the computer-based gaming system 209 may activate an alert. This alert could be conveyed to the user 301 through visual, auditory, and/or haptic feedback via the digital media display device 701.

In response to identifying a potentially unhealthy and/or unhealthy condition 307, the computer-based gaming system 209 may alter 309 the interaction of the user 301 with the digital media 217, in a manner to improve the unhealthy condition. 307

Figure 4:
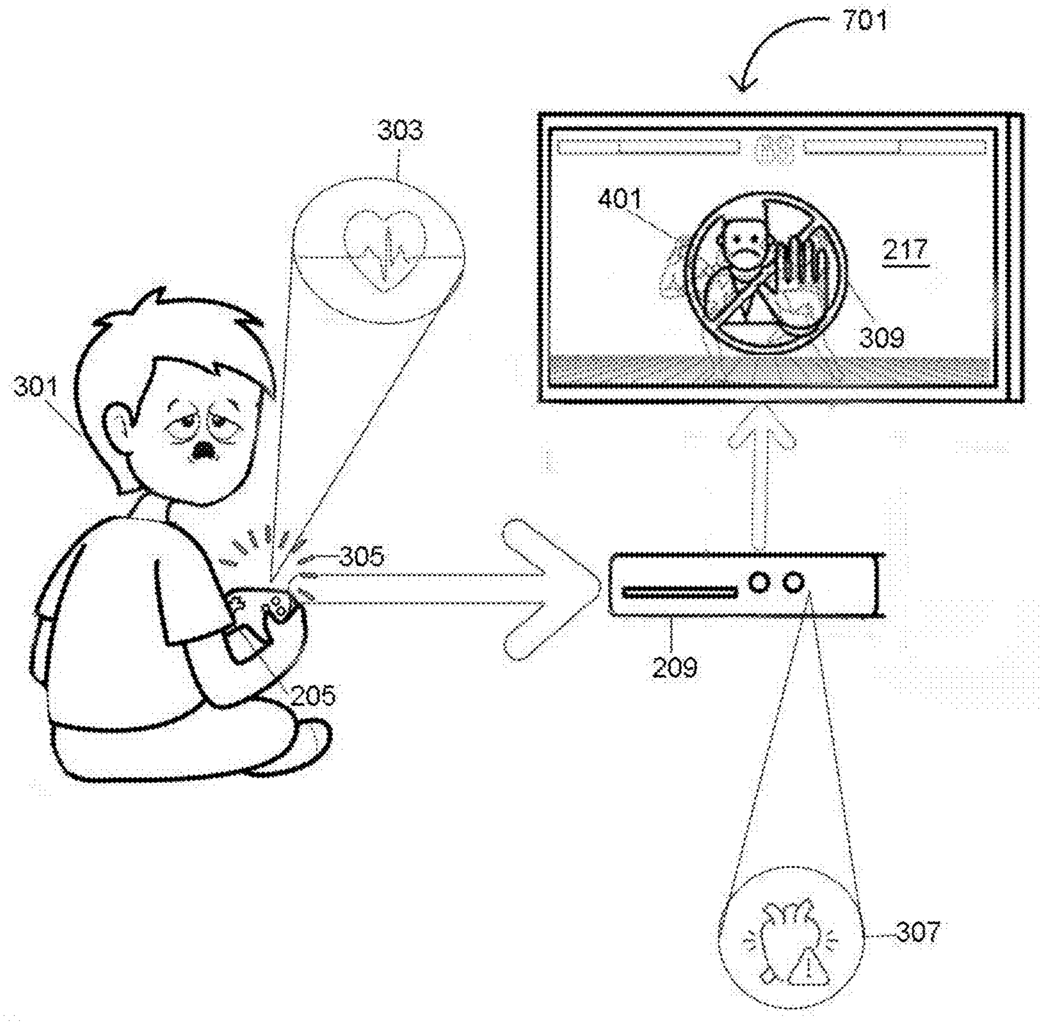
FIG. 4 is an example of a computer based-gaming system altering functionalities to a virtual character in response to a user's unhealthy condition.

FIG. 4 illustrates the response of a computer-based gaming system 209 when it detects an unhealthy condition 307 in a user 301. The user 301 is shown utilizing an input peripheral 205, which is capable of not only registering user inputs but also collecting vital sign information 305, such as heartbeat.

The input peripheral 205 is equipped with sensors that detect and transmit vital sign information 305 to the computer-based gaming system 209 for further analysis.

Upon determining indicators of an unhealthy condition 307 from the analysis, the computer-based gaming system 209 may activate an alert. This alert could be conveyed to the user 301 through visual, auditory, and/or haptic feedback via the digital media display device 701.

Figure 5:
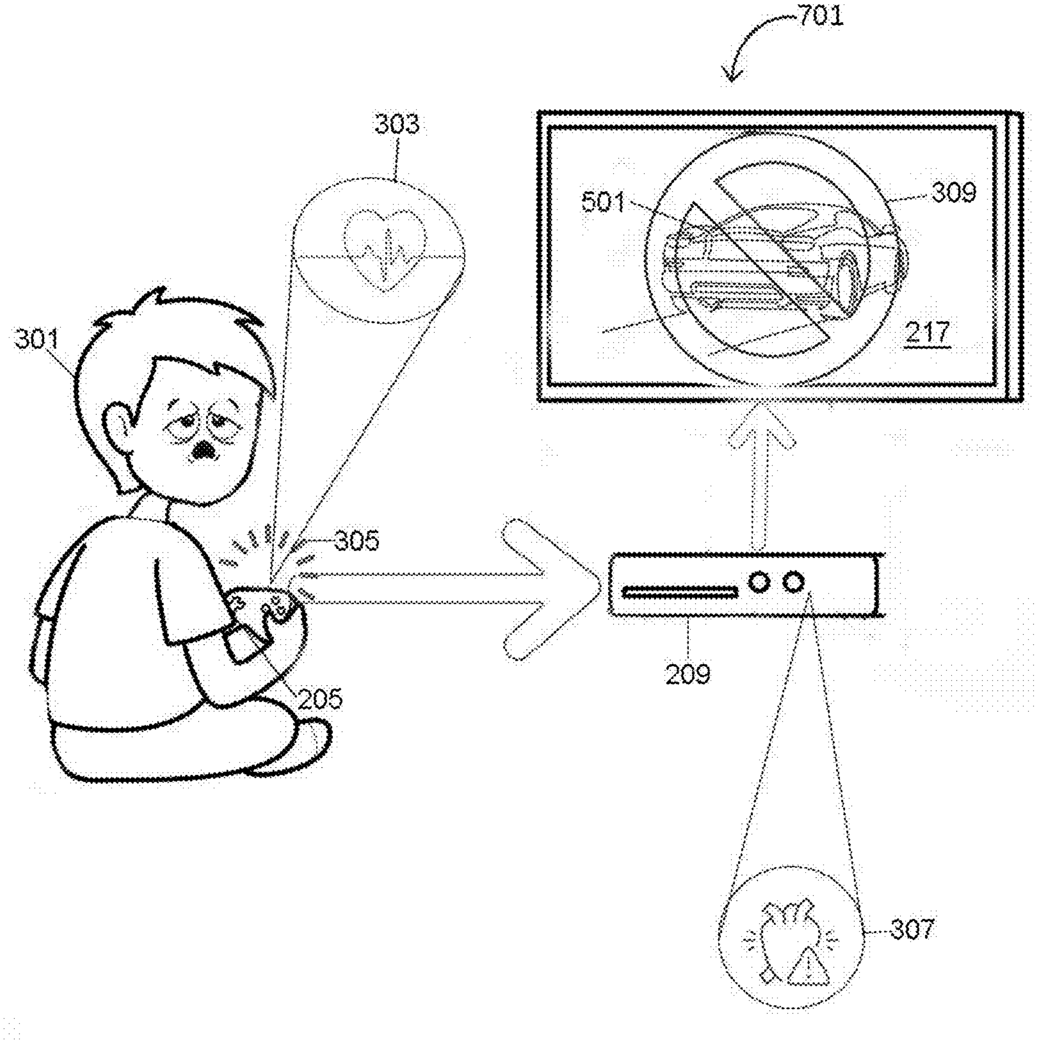
FIG. 5 is an example of a computer based-gaming system altering functionalities to a virtual vehicle in response to a user's unhealthy condition.

In response to identifying a potentially unhealthy and/or unhealthy condition 307, the computer-based gaming system 209 may alter 309 the interaction of the user 301 with the digital media 217, specifically altering 309 the virtual character 401 in a manner to improve the unhealthy condition. 307 FIG. 5 illustrates the response of a computer-based gaming system 209 when it detects an unhealthy condition 307 in a user 301. The user 301 is shown utilizing an input peripheral 205, which is capable of not only registering user inputs but also collecting vital sign information 305, such as heartbeat.

The input peripheral 205 is equipped with sensors that detect and transmit vital sign information 305 to the computer-based gaming system 209 for further analysis.

Upon determining indicators of an unhealthy condition 307 from the analysis, the computer-based gaming system 209 may activate an alert. This alert could be conveyed to the user 301 through visual, auditory, and/or haptic feedback via the digital media display device 701.

In response to identifying a potentially unhealthy and/or unhealthy condition 307, the computer-based gaming system 209 may alter 309 the interaction of the user 301 with the digital media 217, specifically altering 309 the virtual vehicle 501 in a manner to improve the unhealthy condition. 307

Figure 6:
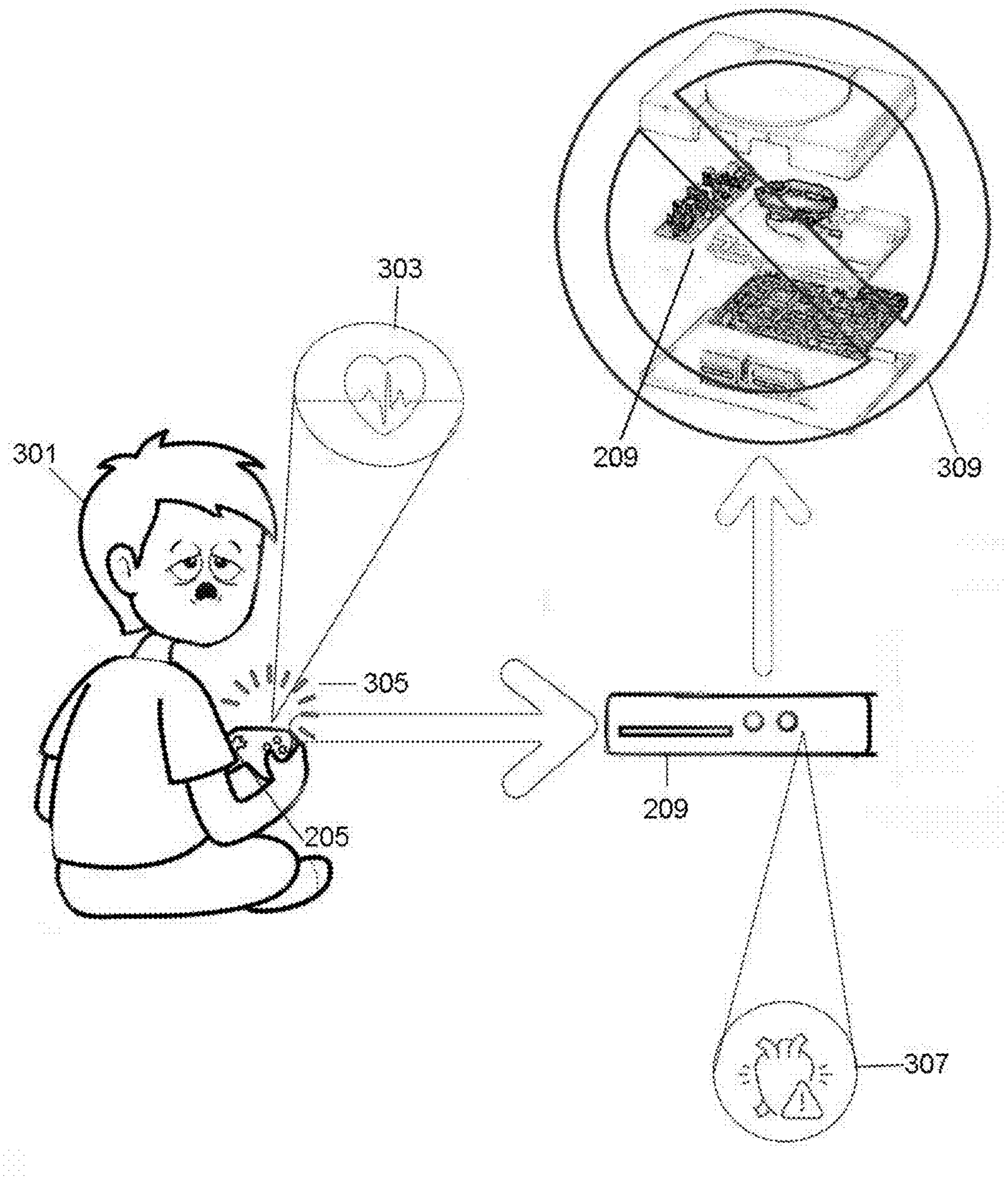
FIG. 6 is an example of a computer based-gaming system altering functionalities to components of a computer based-gaming system in response to a user's unhealthy condition.

FIG. 6 illustrates the response of a computer-based gaming system 209 when it detects an unhealthy condition 307 in a user 301. The user 301 is shown utilizing an input peripheral 205, which is capable of not only registering user inputs but also collecting vital sign information 305, such as heartbeat.

The input peripheral 205 is equipped with sensors that detect and transmit vital sign information 305 to the computer-based gaming system 209 for further analysis.

Upon determining indicators of an unhealthy condition 307 from the analysis, the computer-based gaming system 209 may activate an alert. This alert could be conveyed to the user 301 through visual, auditory, and/or haptic feedback via the digital media display device 701.

In response to identifying a potentially unhealthy and/or unhealthy condition 307, the computer-based gaming system 209 may alter 309 the interaction of the user 301 with the digital media 217, specifically altering 309 the computer-based gaming system 209 in a manner to improve the unhealthy condition 307.

Figure 7:
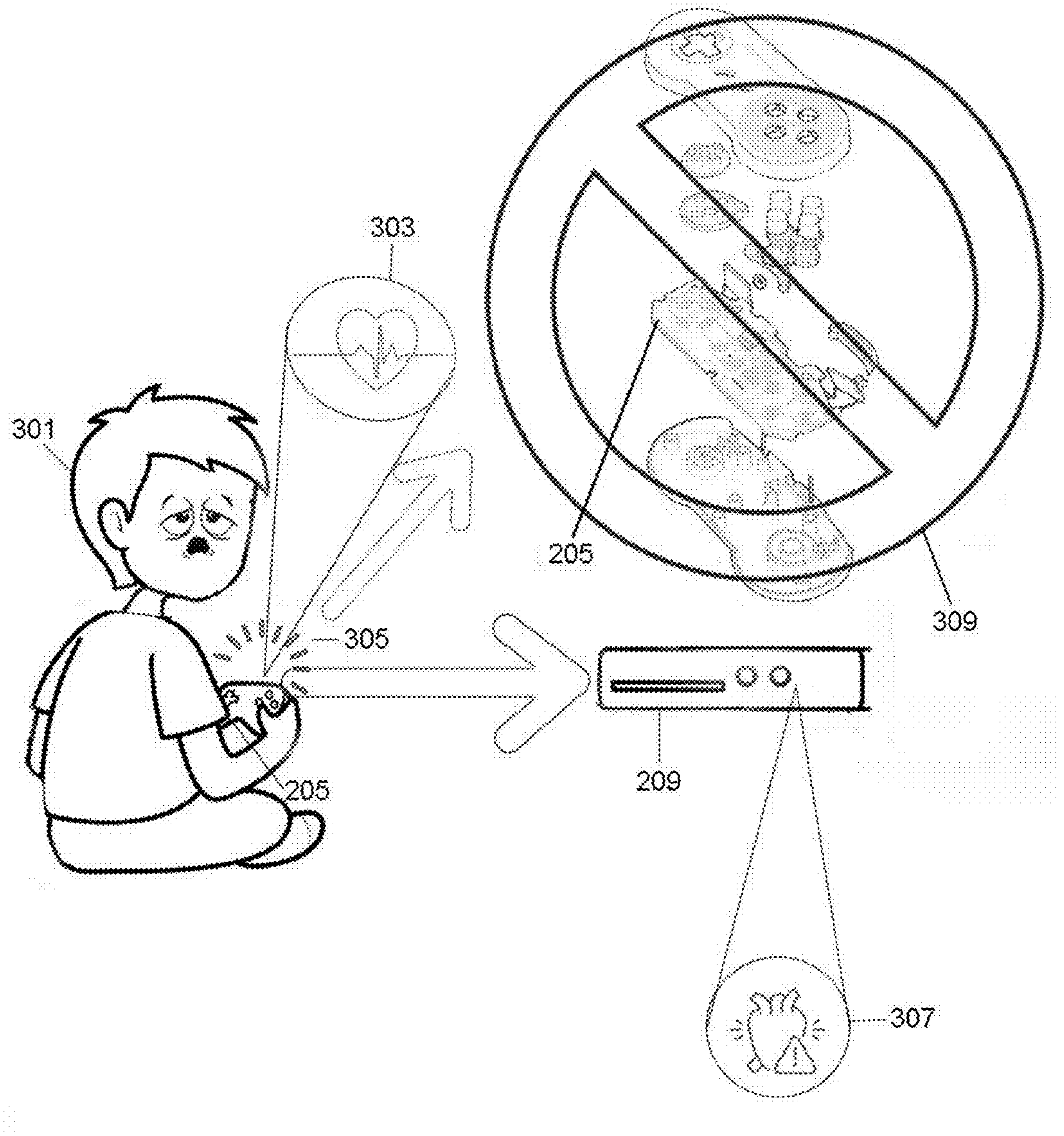
FIG. 7 is an example of a computer based-gaming system altering functionalities to an input peripheral in response to a user's unhealthy condition.

FIG. 7 illustrates the response of a computer-based gaming system 209 when it detects an unhealthy condition 307 in a user 301. The user 301 is shown utilizing an input peripheral 205, which is capable of not only registering user inputs but also collecting vital sign information 305, such as heartbeat.

The input peripheral 205 is equipped with sensors that detect and transmit vital sign information 305 to the computer-based gaming system 209 for further analysis.

Upon determining indicators of an unhealthy condition 307 from the analysis, the computer-based gaming system 209 may activate an alert. This alert could be conveyed to the user 301 through visual, auditory, and/or haptic feedback via the digital media display device 701.

In response to identifying a potentially unhealthy and/or unhealthy condition 307, the computer-based gaming system 209 may alter 309 the interaction of the user 301 with the digital media 217, specifically the input peripheral 205 in a manner to improve the unhealthy condition 307.

The computer-based gaming system 209 may include a feature allowing for customizable display of vital sign(s). A user 301 may be able to customize how their vital sign information 305 and/or vital sign(s) is presented during digital media interaction. This customization may include: Selecting which vital sign(s) are displayed; Choosing the format of the display (e.g., numerical values, graphs, color-coded indicators); Determining the size and position of the vital sign display on the screen; Setting the frequency of updates to the displayed information.

The computer-based gaming system 209 may offer various display styles for vital signs, such as: Minimalist designs that blend with the game interface; Detailed dashboards for comprehensive health monitoring; Thematic displays that match the aesthetic of specific games or genres; Users may also be able to set different display configurations. For example, a user may choose a more detailed display for lengthy gaming sessions and a simpler display for shorter play periods.

The computer-based gaming system 209 may allow users to set custom alerts or notifications based on their vital sign readings. These alerts may be visual, auditory, and/or haptic feedback.

The vital sign display may be toggled on or off at the user's discretion. The computer-based gaming system 209 may also or instead automatically hide the display during intense gameplay moments to avoid distraction, showing it only during calmer periods or when significant changes in vital signs are detected.

For multiplayer games, the computer-based gaming system 209 may offer options to share vital sign displays with other players, with customizable privacy settings to control what information is shared.

The computer-based gaming system 209 may use machine learning and/or artificial intelligence to suggest optimal vital sign display configurations based on the user's gaming habits, health history, and current gameplay context.

The vital sign display customization options may be accessible through an in-game menu, allowing users to adjust their preferences without leaving the gaming environment.

The computer-based gaming system 209 may also or instead provide an option to export vital sign data in various formats for external analysis or sharing with healthcare providers.

The computer-based gaming system 209 may include a feature that shows vital signs improving in real time.

This real-time display may visually represent the positive changes in the user's vital signs as they occur, providing immediate feedback on the effectiveness of alterations or user-initiated health improvement techniques.

The computer-based gaming system 209 may present this information through various visual formats, which may include: graphs or charts that may update continuously; Color-coded indicators that shift as vital signs move into healthier ranges; Numerical values that change in real time; and visual representations of the body or specific organs affected by the improving vital signs.

The real-time improvement display may be integrated into the digital media and/or external device such as a cellphone, or smartwatch.

The computer-based gaming system 209 may highlight significant improvements, possibly through visual or auditory cues.

In multiplayer scenarios, the computer-based gaming system 209 may allow users to share their vital sign improvement data with team members, potentially fostering a cooperative approach to health management during gameplay.

The computer-based gaming system 209 may use this real-time improvement data to adjust its alteration strategies.

The computer-based gaming system 209 may also or instead gamify the vital sign improvement process, possibly offering and/or giving in-game rewards or achievements for sustained health improvements. And after offering the reward, applying a cooldown period during which, no other rewards are offered and/or given to the user until after the cooldown period has elapsed. There may also be a predetermined maximum number of times in game rewards are offered this way.

Users may be able to customize which vital signs they want to monitor for improvement and how they want this information displayed.

The computer-based gaming system 209 may provide an option to record and review vital sign improvement data over time, allowing users to track their progress across multiple gaming sessions.

FIGS. 3-7 are meant to be illustrative to show how the computer-based gaming system 209 may alter 309 a user's 301 interaction with the digital media 217 in a manner to improve the unhealthy condition 307. Although only heartbeat was illustrated in FIGS. 3-7, as the detected unhealthy condition 307 alterations 309 may be caused by other unhealthy conditions 307 in a user 301 such as respiratory rate, temperature, EEG readings, and blood pressure to name a few.

Figure 8:
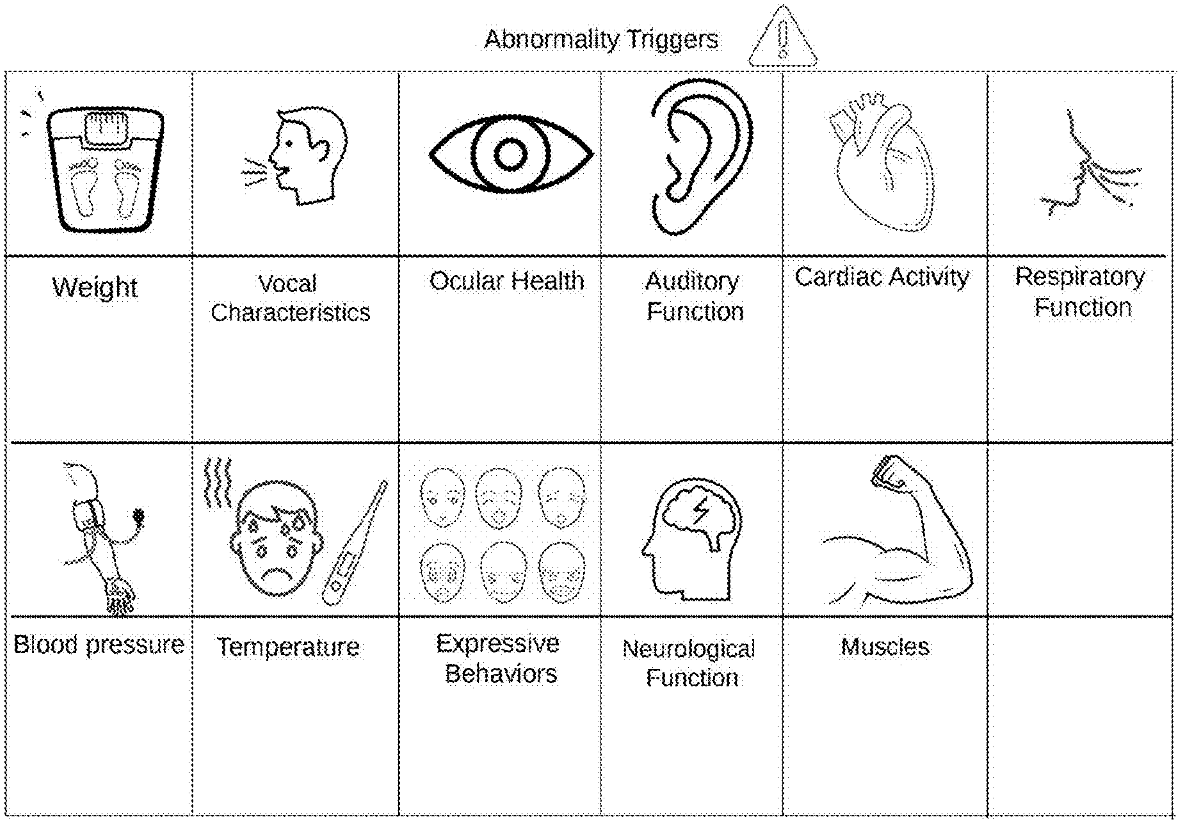
FIG. 8 is an example of a table of triggers that consist of unhealthy conditions that may cause a computer-based gaming system and its associated components to alter their functionalities.

FIG. 8 illustrates a variety of physiological, psychological, biometric and behavioral health metrics that the vital sign detector 207 may be designed to detect. These health metrics, if indicative of a potentially unhealthy and/or unhealthy condition 307, may trigger the computer-based gaming system 209 to alter 309 the user's 301 interaction with the digital media 217

An illustration representing 'Weight' may signify the computer-based gaming system's 209 capability to monitor for deviations from healthy weight ranges, which may include extreme weight loss or gain. The system may track such trends, offering early warnings and facilitating timely health interventions.

The 'Vocal Functions' visual may denote voice irregularities, including vocal cord conditions, speech quality issues, tone of voice, and certain words being spoken.

'Ocular Health' may denote such as visual impairments or ocular diseases which includes eye movement.

'Auditory Function' may denote ear and hearing health, including the identification of harmful sound exposure levels and the detection of conditions resulting from such exposure.

'Cardiac Activity' may denote monitoring for a spectrum of heart-related health issues, ranging from rhythm irregularities and structural heart conditions to coronary and inflammatory heart diseases, potentially impacting cardiac function.

'Respiratory Function' may denote a array of respiratory health issues, from oxygenation and ventilation problems to respiratory infections.

'Blood Pressure' may denote hypertension and hypotension, as well as related cardiovascular health concerns that may affect the user's well-being.

'Temperature' may denote issues related to the body's heat regulation, such as overheating (hyperthermia) or excessive cooling (hypothermia).

'Expressive Behaviors' may denote signs of emotional, psychological, and/or physical distress through facial expressions, sweat, and body language, potentially indicating stress, anxiety, depression, or other emotional disturbances.

'Neurological Function' may denote neurological conditions that may manifest as cognitive impairments, motor function issues, or other neurological anomalies such as epilepsy.

The computer-based gaming system 209 may integrate data from multiple triggers to determine the presence of an unhealthy condition. 307

Figure 9:
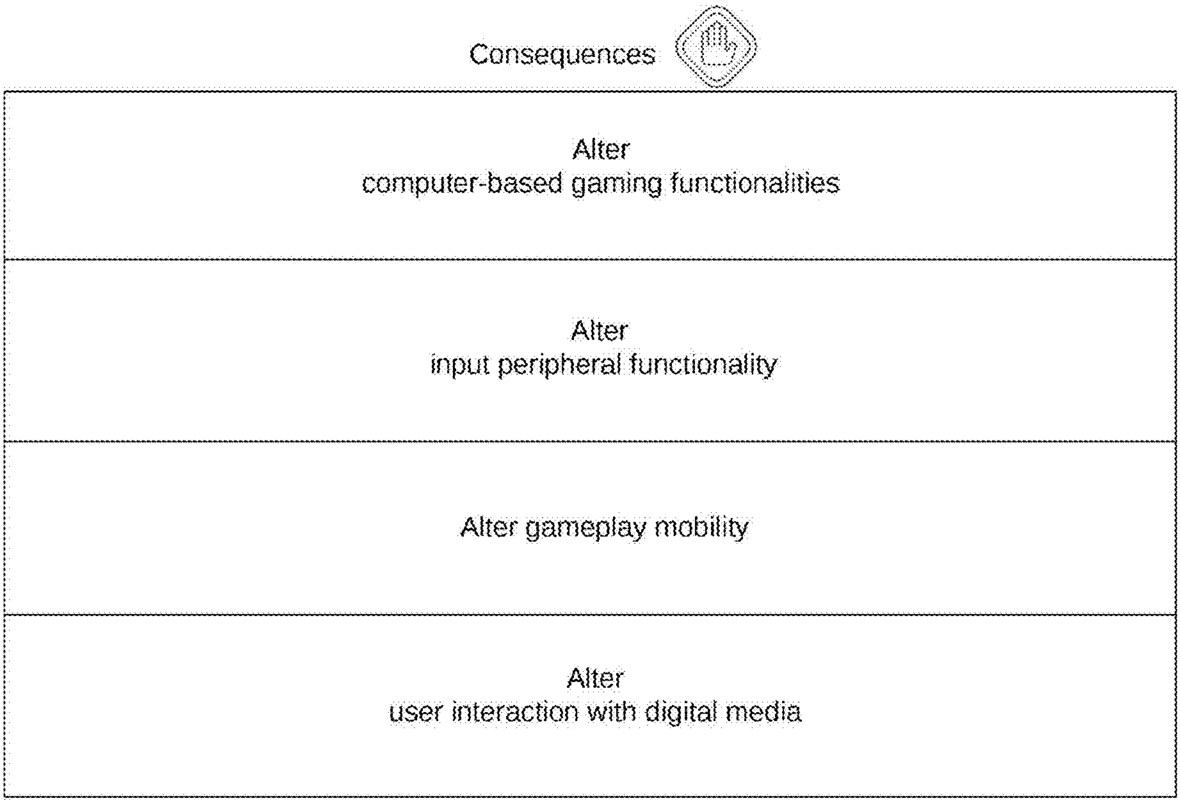
FIG. 9 is an example of a table of consequences that may occur in response to a computer based-gaming system detecting an unhealthy condition in a user.

FIG. 9 illustrates a table outlining potential consequences that may be enacted by the computer-based gaming system 209 upon detecting a potentially unhealthy and/or unhealthy condition 307 in a user 301, based on the analysis of physiological, and/or psychological, and/or behavioral and/or biometric health metrics. The table displays various consequences, including altering computer-based gaming functionalities, altering input peripheral functionality, altering gameplay mobility, and altering user interaction with digital media in a manner that is likely to improve the unhealthy condition 307. Cooldown periods may be applied after an alteration is completed or after a user's vital sign information improves. Cooldown periods may be applied instantly when an alteration is completed, or a select time period after the alteration is completed. During this cooldown period, no further alterations may be made in response to an unhealthy condition until after the cooldown period has elapsed. There may be a maximum number of times the computer-based gaming system 209 may apply alterations. The maximum number of alterations may be select, predetermined, or predefined. The number of maximum alterations, the duration of the cooldown period, or the alterations themselves may be communicated to the user through visible or auditory indicators. These indicators may provide feedback to the user about the system's current status, such as how many alterations remain available, how long the cooldown period will last, or the nature of the applied alterations.

Methods and/or processes for implementing these alterations and/or how alterations may be obtained, managed, tailored, customized, used, and/or prepared in response to an unhealthy condition 307 and/or potentially unhealthy condition and the nature of alterations 309 such as how they may be able to regenerate, are described in the subsequent paragraphs below.

The computer-based gaming system may include a feature to initiate emergency calls, such as 911, in scenarios where an unhealthy condition 307 is detected in the user. 301 This capability may allow the computer-based gaming system 209 to contact emergency services that may require immediate medical attention.

The computer-based gaming system, 209 may also utilize methods involving machine learning and/or artificial intelligence (AI), and/or pattern recognition, and/or algorithms to adapt the gaming experience. This adaptation may include the system's response to the user's 301 reactions to specific game elements or outcomes. The AI may alter 309 the gaming experience in real-time, potentially modifying game dynamics, content, or providing helpful suggestions. For example, the computer-based gaming system 209 may alter 309 the game in response to certain game content and/or elements and/or or due to repeated challenges. The AI's decision-making may be informed by an analysis of the user's historical interaction data and current gaming session, which may enable personalized game alterations 309 responsive to the user's 301 health.

As an example, if a user 301 is playing a video game and consistently exhibits increased and/or decreased vital signs, in response to an element like a spider on the screen, the computer-based gaming system 209 may suggest the possibility of a condition like Arachnophobia and offer real-life recommendations for addressing it. The computer-based gaming system 209 may also or instead propose in-game option(s) to alleviate the user's condition, such as removing certain elements (such as the spider) or allowing the user to skipping levels that contain elements that negatively influence the users 301 overall health.

If an unhealthy condition 307 is detected, alterations 309 may not be made until after a cooldown period. After the cooldown period, the system may make the necessary alteration 309, whether or not the unhealthy condition 307 still persists. For example, if a user 301 has a preset condition such as arachnophobia or if this condition becomes apparent during digital media interaction, the system may act accordingly. Suppose a user 301 is playing an RPG game, and an unrelated alteration 309 triggers a cooldown period. During this cooldown period, if the user 301 encounters spiders in the game, and the preset condition is arachnophobia, the system may implement alteration(s) 309 only for the one or more preset conditions, thus overriding the cooldown period.

If the arachnophobia condition was not preset and an unhealthy condition 307 is detected during the encounter (e.g., the user 301 runs from or eliminates the spiders, leading to improved vital signs), the system may still alter future game interactions involving spiders, even if the immediate unhealthy condition 307 has improved. This may be done by altering the game's memory so all spiders in the game are now rats. The user may choose what the spiders are changed to or the alteration may be based on predefined information such as computer code for example that allows spiders turn into rats or cows if unhealthy condition 307 is present. The system may then diagnose the user 301 with arachnophobia and preset this condition for future digital media interaction alterations to prevent the unhealthy condition 307 from being triggered again.

Alterations 309 may be formed and/or transferred not only from a computer-based gaming system 209, but from and/or to various devices. These devices may include but it's not limited to, smart watches, smart glasses, VR headsets, AR headsets, MR headsets, television consoles, and computer-based gaming systems 209 and other digital media interaction systems. These devices may facilitate real-time alterations 309 during the user's interaction with digital media 217, similar to the real-time alteration process described for VR systems in FIG. 11. In some implementations, alterations 309 may be transferred to one or more of these devices, which may have its own architecture such as illustrated in FIG. 2 to operate independently without requiring interaction with a computer-based gaming system 209.

Another aspect of AI utilization in the computer-based gaming system 209 may involve learning from the user's 301 behavioral patterns and/or physiological and/or psychological and/or biometric responses during gameplay. This may include the computer-based gaming system's 209 analysis of reactions to in-game events and/or game elements, whether specific or varied. Based on this data, the AI may adapt the gaming experience, potentially modifying game dynamics, and/or content, and/or providing strategic tips to the user 301. The AI's decision-making process may be informed by an analysis of the user's 301 historical interaction data and/or current gaming session, which may provide personalized game alterations 309.

For example, consider a scenario where the user is playing a computer-based gaming system 209 such as a slot machine. The computer-based system 209 may detect an increase in the user's heart rate and/or signs of frustration when the user sees and/or locks in one or two sevens in a row. In response, the AI may offer strategic tips and/or alter 309 the game. The computer-based gaming system 209 may also alter 309 the users 301 interaction with the digital media 217 in a way such as the odds of winning, to facilitate a more positive outcome. To ensure fairness and/or security measures, the computer-based gaming system 209 may include technologies like facial recognition and fingerprint identification, limiting this assistance to a predetermined number of times per user, with the possibility of utilizing a set cooldown period. This measure may be in place to prevent a user from abusing this assistance.

The computer-based gaming system 209 may also include a feature for providing in-game directions to the user. Utilizing AI, and/or machine learning, and/or pattern recognition technology, the computer-based gaming system 209 may analyze in-game events to determine the need for assistance. The computer-based system 209 may then offer directions or suggestions within the game, which may be tailored to the user's 301 current situation and gameplay progress.

For instance, in a scenario where a user is playing an adventure game and exhibits signs of frustration and/or confusion, the computer-based gaming system 209 may recognize that the user 301 is having trouble finding their way. In response, the AI may provide in-game hints and/or directional guidance to help the user navigate the game environment. This assistance may be based on an analysis of the user's current location in the game, and/or their gameplay history, and/or the in-game challenges they are facing.

The computer-based gaming system 209 may also include a feature that suggest actions to the user during gameplay. The computer-based gaming system 209 may guide the user on actions they should take, which may include pressing certain buttons whether in combination with one another or by themselves on the controller and/or performing specific movements with external motion-sensing devices. Depending on the context of the game and the user's 301 interaction with the game environment and/or input peripheral 205, the computer based-gaming system 209 may adapt its suggestions.

The computer-based gaming system 209 may also include features to alter 309 in-game resources and/or game mechanics. This may involve replenishing in-game resources such as items and/or health, and/or mana, and/or similar resources that enable the user 301 to perform various actions within the game. The computer-based gaming system 209 may also or instead alter 309 game mechanics to assist the user. These alterations 309 may include, but are not limited to, enabling the user to jump higher, increasing the user's speed, enhancing aiming stability and accuracy, or increasing attack power to facilitate easier progression through the game.

Additionally, the computer-based gaming system 209 may alter certain game mechanics based on the user's 301 condition. For example, in a racing game, the computer-based gaming-system 209 may alter 309 the difficulty of executing maneuvers like drifting, making them easier to perform.

The computer-based gaming system 209 may also offer the user the option to skip a level and/or proceed directly to the next stage and/or cutscene of the game. This feature may allow the user to bypass challenging game segments.

The computer-based gaming system 209 may also include features that reduce(s) events of a game and/or the user's required effort for a game. These features may activate when the system detects an unhealthy and/or potentially unhealthy condition 307 in the user, 301.

Reducing the events of the game may involve decreasing the frequency and/or intensity of in-game challenges, and/or encounters, and/or tasks.

Similarly, the feature to reduce the user's required effort may alter the level of physical or mental engagement needed to progress in the game. This may include simplifying controls, and/or reducing the complexity of tasks, and/or providing additional in-game assistance.

The computer-based gaming system 209 may also integrate with massage technology embedded in gaming chairs and/or wearable devices such as neck braces, and/or wrist braces and/or hand braces. The computer-based gaming system 209 may trigger the massage functions in these devices that may help relieve stress and/or fatigue and/or pain and/or discomfort in a user 301 by providing physical comfort to the user 301 during gaming sessions.

The computer-based gaming system 209 may also be capable of altering 309 the environment around the user. 301 This may include changes in lighting, which could be altered 309 to create a more comfortable and less straining atmosphere for the user. 301 The computer-based gaming system 209 may also or instead modulate the intensity and/or color, and/or pattern of the lighting, Additionally, the computer-based gaming system 209 may also interface with climate control devices such as heaters, and/or fans, and/or air conditioning units, and/or heating units. The computer-based gaming system 209 may turn these devices on or off, and/or alter 309 their settings to higher or lower levels, and/or potentially even altering 309 the thermostat settings.

The computer-based gaming system 209 may also include a feature to slow down on-screen animations and/or movements, this slowing down of visual elements may involve reducing the speed of animations, transitions, or other dynamic aspects of the game. This may aid in lowering seizures and/or discomfort in users 301 who might be sensitive to rapid or flashing visuals.

The computer-based gaming system 209 may also include a feature to alter 309 the pixels being presented on the screen. The computer-based gaming system 209 may alter 309 the pixel presentation, which could involve changes in color balance, brightness, contrast, and/or the introduction of filters.

In addition to altering 309 visual elements, the computer-based gaming system 209 may alter 309 the pixels on the screen to display messages to the user. The computer-based gaming system 209 may display messages that inform the user of their current health status and/or provide suggestions for actions the user may take to possibly mitigate any identified unhealthy and/or potentially unhealthy conditions.

The computer-based gaming system 209 may also include input peripherals 205 integrated with heating and/or cooling functionalities, designed to warm or cool the user's hands. The heating and/or cooling functions in the input peripherals 205, such as game controllers, keyboards, and/or mice, can be activated to provide thermal comfort to the user. 301 The computer-based gaming system 209 may alter 309 the temperature of these input peripherals 205 based on real-time analysis of the user's physical state and/or environmental conditions. For example, during prolonged gaming sessions in cold conditions, the system may activate the heating technology to maintain optimal hand temperature, while in warmer conditions, the cooling function may be employed to prevent overheating and discomfort.

The computer-based gaming system 209 may also be configured to alter 309 a running task and/or a program such as a game program. This feature ensures that the user's well-being is prioritized.

Additionally, the computer-based gaming system 209 may be designed to execute certain programs or tasks, such as game launchers or digitally downloaded games, only when it detects that the user's conditions are healthy. This may involve a preliminary health check before initiating a task and/or program.

The computer-based gaming system 209 may also be configured to achieve full functionality only after verifying that the user's 301 vital signs 303 fall within a healthy range. This configuration may encompass a health check mechanism that evaluates the user's 301 vital signs 303. Depending on the results, the computer-based gaming system 209 may restrict or limit access to certain functionalities of the computer-based gaming system 209 until the user's 301 health condition is deemed suitable for gaming.

The computer-based gaming system 209 may also include a feature capable of deactivating the vital sign detector's 207 influence on gameplay. This feature may be applicable in scenarios wherein gameplay mechanics are directly linked to monitoring a user's 301 vital signs 303. In situations where continued gameplay and/or use, is influenced by these vital signs 303, the system may decouple gameplay and/or functionalities of the computer-based gaming system 209 from the vital sign 303 inputs. This decoupling may result in an alteration 309 in the interaction between the computer-based gaming system 209 with the vital sign inputs, while monitoring of the vital signs 303 continues. Thus, despite the temporary suspension of the vital signs 303 data's direct impact on gameplay, the computer-based gaming system 209 may remain active in monitoring the users 301 vital signs 303.

The computer-based gaming system 209 may also include a feature to alter 309 the difficulty of a game. This alteration 309 may involve altering 309 various aspects of the game's challenge, such as enemy difficulty, puzzle complexity, or time constraints, depending on the specific game and situation. The computer-based gaming system 209 may implement this change to provide a more tailored gaming experience that may align with the user's 301 current health condition.

The computer-based gaming system 209 may also offer online functionalities wherein gameplay may be contingent upon the detection of healthy vital signs 303 from each participating user. 301 In such online gaming scenarios, the computer-based gaming system 209 may analyze the vital signs 303 of all users 301 involved, using this data to adapt the gameplay. The computer-based gaming system 209 may alter 309 the game's pace, difficulty, or other elements to ensure a health-conscious gaming environment for all users. 301

In addition to offering online play, the computer-based gaming system 209 may alter 309 user 301 interactions in online sessions. The computer-based gaming system 209 may modify a way in which a user 301 participates. This may involve altering 309 competitive elements, and/or offering collaborative gameplay and/or alternatives, and/or temporarily restricting interaction to manage the user's 301 health. The computer-based system 209 may also or instead actively monitor multiplayer interactions, providing support and/or intervention.

The computer-based gaming system 209 may also alter 309 multiplayer play. Alterations 309 may include modifying gameplay intensity, offering collaborative options, and/or limiting user interaction as appropriate.

The computer-based gaming system 209, may also alter 309 the user's 301 interaction with the digital media 217 such as a video game by removing, and/or restricting, and/or prohibiting a user's participation in a multiplayer gaming session. In such instances, the computer-based gaming system 209 may substitute and/or replace the user-controlled player with a computer-controlled player, known as a CPU. This substitution and/or replacement may ensure gameplay continuity while prioritizing the user's 301 health.

This computer-controlled player (CPU) may be configured to match the skill level of the user-controlled player it is replacing, and/or to align with the skill level of at least one other user-controlled player and/or computer-controlled player in the gaming session. Alternatively, the computer-controlled player may possess a skill rating that is below, equivalent, or above the overall skill level of the gaming lobby. Upon an improvement in the users 301 health status, the system may remove the computer-controlled player (CPU) and allow the user 301 to resume operations of their user-controlled player and/or position in the game.

A user 301 may be able to design the computer-controlled player to play in a certain manner. The gameplay patterns of the computer-controlled player may be custom built by the user 301. The gameplay patterns may also be mimicked by the user 301 themselves and/or other users based on previous gameplay. This feature may also work in solo games that are not multiplayer. When one or more users are in an online game, the user(s) gameplay information patterns may be received and stored by a computer-based gaming system 209 and/or a host system 201. This gameplay information may be used to train the computer-controlled player.

The computer-based gaming system 209 may also communicate with the host system 201 to alter 309 a user's 301 online gaming capabilities. This alteration 309 may include modifying, limiting, or suspending the user's 301 participation in online gameplay. The host system 201 may implement these measures based on data from the computer-based gaming system 209, aligning the user's 301 participation with a health-conscious gaming environment.

Additionally, the computer-based gaming system 209 may restore the user's 301 online playing privileges upon detecting an improvement in their potentially unhealthy and/or unhealthy condition, 307 indicating a return to a healthier state.

The computer-based gaming system 209 may also alter 309 audio outputs. This alteration 309 may include altering 309 overall sound levels, changing music tracks, or delivering audio messages to the user. 301 Such alterations 309 in audio could include, but are not limited to, reducing the volume to minimize auditory strain, and/or playing calming music and/or providing verbal suggestions or guidance through the game's audio system. The computer-based gaming system 209 may alter 309 these audio elements based on real-time analysis of the user's health data.

In addition to individual audio alterations 309, the computer-based gaming system 209 may also convey messages to other players regarding a user's 301 condition. The computer-based gaming system 209 may generate audio messages informing other players in the gaming session. This may include notifications about the affected user's current state and/or suggestions for cooperative gameplay alterations 309 that may help accommodate the user's 301 health needs.

The computer-based gaming system 209 may also record data related to gameplay sessions that lead to and/or or leads to a potentially unhealthy and/or unhealthy conditions 307 in users. 301 The system may utilize this data to inform a user 301 recommendations in a digital store environment.

For example, say a user 301 exhibits an increased heart rate and/or stress while playing a horror game(s), the computer-based gaming system 209 may recommend against similar games in the digital store. This feature may help in guiding users 301 towards choices better aligned with their health profile.

Furthermore, the computer-based gaming system 209 may also or instead provide a customized game browsing section, tailored to a user's 301 vital sign information.

The computer-based gaming system 209 may also collect and/or analyze gameplay data and/or digital media interaction data to determine correlations between specific games and/or digital media and the onset of an unhealthy condition 307 in a user 301. This data may be displayed in a digital game store, and/or on the user's 301 digital media 217 providing insights into how certain games and/or digital media 217 have affected the health of other players and/or users. This information may also be displayed when a user 301 connects to another user via share play and/or share screen technology.

For each game and/or other form of digital media 217, the computer-based gaming system 209 may present statistics and/or findings showing the prevalence of various unhealthy conditions 307 experienced by users. This data may be shown on the game's store page, and/or on the user's 301 digital media 217 which may give potential buyers and/or consumers an overview of the game's and/or digital media health impact history.

The computer-based gaming system 209 may then compare these findings with the health profile of the individual user 301. If a game and/or other form of digital media 217 is known to frequently cause potentially unhealthy and/or an unhealthy condition 307 that may align with the user's 301 known health vulnerabilities, the computer-based gaming system 209 may advise against purchasing and/or playing the game and/or other form of digital media 217. The computer-based gaming system 209 may also or instead prepare the digital media 217 to have pre-applied alterations 309 that may prevent an unhealthy condition 307 in the user 301 from arising. For example, a user 301 has an unhealthy condition 307 indicative of epilepsy. The user 301 may want to purchase and/or play a fast-paced rhythm video game from the online digital media 217 store. The computer-based gaming system 209 which may already be aware of the user's 301 unhealthy condition 307, may pre-apply alterations 309 to the digital media 217 in a manner to prevent the unhealthy condition 307 from arising. This may be done by reducing the speed of the notes the user 301 has to hit in the rhythm game. This pre-applied alteration 309 may be downloaded with the game files of the rhythm game. The pre applied alteration 309 may also already be set on the user's 301 computer-based gaming system 209 so when the game is started, the alterations 309 may be applied. This recommendation process may use explicit warnings, suggestions for alternative, healthier gaming options, or even restrictions on purchasing games deemed particularly risky for the user's 301 health.

In cases where a user's 301 health profile suggests a high risk of experiencing a specific unhealthy condition 307, the computer-based gaming system 209 may restrict the purchase and/or access to certain games. This preventive measure may be applied during browsing games and/or other forms of digital media 217 in the digital store and/or on the internet, viewing shared gameplay like share play and/or share screen, watching videos of the game and/or other form of digital media 217 while using the computer-based gaming system 209 as the device to access the videos and/or other form of digital media 217 content and/or even when considering a game and/or other form of digital media 217 content recommended by other users.

The computer-based gaming system 209 may incorporate ejection mechanisms that may work independently or in conjunction with locking mechanisms. Such ejection mechanisms may be designed to automatically eject physical game media, such as ROM (read only memory) cartridges, Game cartridges, compact discs, or other game storage formats, in response to detected unhealthy conditions. The computer-based gaming system 209 may also include a disc drive and/or cartridge reader slot equipped with a locking mechanism. This feature may prevent the insertion of physical game media to the extent necessary for the system to recognize and execute the game.

The computer-based gaming system 209 may be configured with software and/or firmware that selectively allows or prevents game execution based on the user's health status. This includes cases where a game, whether in physical media form such as ROM cartridges, and/or Game cartridge, and/or compact discs, and/or digital format stored on hard drives, solid-state drives, or external storage devices, is ready to be played. The system may perform a health check, following the process outlined in the flowchart of FIG. 1, before allowing the game to run. The execution of the game, regardless of its format, may only proceed if the health check confirms that the user's conditions are healthy.

The input peripherals 205 may be configured with hardware, software, and/or firmware to alter 309 functions such as button presses, joystick movements, or other interactive elements.

This may include a physical mechanism to block or lock input commands. For instance, a sliding cover or clamp might be employed, actuated by a solenoid to move into position, thereby preventing operation of the input controls.

Moreover, the locking mechanism may be remotely controlled via wireless communication technologies like Bluetooth, Wi-Fi, or radio frequency (RF), receiving signals from devices such as smartphones, computers, or gaming consoles to activate and/or deactivate the lock.

The actuator may be an integrated wireless device, housing both the mechanical locking components and the communication module, and capable of executing lock/unlock commands received from the gaming system.

Additionally, the motion of the input peripheral 205, such as a computer mouse and/or motion-sensing device, and/or controller. may be altered 309 as well.

The input peripheral, 205 whether integrated with and/or separate from the computer-based gaming system, may be configured to include locking mechanisms. These mechanisms may be designed to prevent and/or restrict the physical depression of buttons on a range of devices including but not limited to game controllers, computer mice, or keyboards. It may also restrict the movement of an analog stick, and/or joystick and/or lever. Furthermore, the software and/or firmware of the input peripheral may be adapted so that, even if a button is physically pressed, the input may not necessarily be registered by the system. This alteration 309 may serve as a potential intervention to pause gameplay, which may prompt the user to address their health condition before continuing. Such features may ensure the safety and well-being of the user under various conditions. This mechanism may be implemented to physically block and/or lock the buttons and/or lever and/or joystick of an input peripheral 205 This may be a sliding cover, a clamp, or any other structure that may be moved into place to prevent the button from being pressed. A solenoid may serve as the actuator for this task. Upon activation, the solenoid may move the locking mechanism into place, and upon deactivation, it retracts the mechanism, allowing free use of the buttons.

The input peripheral, 205 may also have a feature wherein, if a user successfully presses a button and/or or engages with a lever and/or analog stick that may be equipped with the input peripheral 205, the inputs may not be registered by the system in response to an unhealthy condition detected in the user.

In addition to manual operation, this locking mechanism may be controlled remotely. The input peripheral 205 may be equipped with a wireless communication module, such as Bluetooth, Wi-Fi, or RF, enabling it to receive signals from an external device, which could be a smartphone, computer, or gaming console. When this module receives a specific command, it may trigger the solenoid to activate or deactivate the locking mechanism.

Furthermore, the actuator itself may be designed as a self-contained wireless device that directly communicates with the game controller. This integrated actuator may house both the mechanical components needed for the locking action and a built-in wireless module. When it receives a signal from an external device, the actuator may execute the command to lock and/or unlock the buttons.

The input peripheral 205 may also be altered 309 in a way wherein the movement of an input peripheral 205.

The computer-based gaming system 209 may also alter 309 the video games virtual environment. For example, in a scenario where a player is repeatedly failing to complete a challenging jump onto a hill, and/or led, the computer-based gaming system 209 may alter 309 the height of the hill and/or ledge within the virtual environment, making the task more achievable.

Users 301 may input a specified time duration for which they will interact with the digital media 217 on the system. Based on this inputted duration, the system may determine the number of alterations that the computer-based gaming system may apply in response to an unhealthy condition, and after this time period, no further alterations may be applied even if an unhealthy condition is detected. The time of which the user 301 may interact with the digital media 217 may also determine the number of alterations 309 for that digital media interaction session. Users 301 may also choose not to input a specific time; in such cases, an alteration 309 may become available after a select time period of digital media 217 interaction.

The computer-based gaming system 209 may incorporate an AI feature that teaches and/or suggests techniques to the user to improve their unhealthy condition 307.

For example, the computer-based gaming system 209 may suggest techniques such as taking deep breaths when it detects an unhealthy condition 307 and/or potentially unhealthy condition in a user 301.

The computer-based gaming system 209 may not proceed with digital media interaction from a user 301 or entirely until it detects that the user 301 is actively performing the suggested techniques and/or until the unhealthy condition 307 and/or potentially unhealthy condition has improved. This detection may be accomplished through various means, such as: Monitoring respiratory rate through integrated or connected sensors, analyzing audio input to detect breathing patterns, using camera input to observe user movements indicative of the suggested technique, tracking changes in other relevant vital sign(s) that may be influenced by the suggested technique.

The computer-based gaming system 209 may include a duration-based alteration 309 feature. This feature may alter 309 a user's 301 interaction with the digital media 217 for a select time period. The time period may be predetermined and/or select. The duration of the alteration 309 may be based on the type of unhealthy condition 307 detected and/or the severity of the condition.

Example: The computer-based gaming system 209 may detect when a user's 301 body temperature is above or below a threshold that may indicate an unhealthy condition 307 and/or potentially unhealthy condition. The user 301 may set their own temperature thresholds on the computer-based gaming system 209 and/or the computer-based gaming system 209 may use machine learning and/or artificial intelligence to determine when a user 301 may experience an unhealthy condition 307 and/or potentially unhealthy condition based on their body temperatures being above or below a threshold. When a user's 301 temperature is above a threshold, the computer-based gaming system 209 may determine how long it needs to turn on a fan, at what intensity the fan level should be, and may be able to detect the distance of the user 301 from the fan to make this determination.

The computer-based gaming system 209 may determine the duration of the alteration 309 through various methods. It may use a preset time period for each type of unhealthy condition 307 and/or potentially unhealthy condition. The computer-based gaming system 209 may also or instead calculate the duration based on the degree of deviation from healthy vital sign ranges.

The alteration 309 may persist for the determined time period. The computer-based gaming system 209 may then reassess the user's 301 vital sign information 305. If the unhealthy condition 307 and/or the potentially unhealthy condition persists, the computer-based gaming system 209 may extend the alteration 309 duration period. If the user's 301 unhealthy condition 307 and/or potentially unhealthy condition improves, the computer-based gaming system 209 may terminate the alteration 309 and/or gradually or immediately return what was altered 309 to its original state.

The duration of the duration-based alteration 309 may be determined based on the unhealthy condition 307 and/or potentially unhealthy condition, and/or the time it may take for the unhealthy condition 307 and/or potentially unhealthy condition to be improved. For example, say the users body temperature is above a threshold that is indicative of an unhealthy condition 307 and/or potentially unhealthy computer-based gaming system condition. The duration-based alteration may be determined based on: the current temperature of the environment the user 301 is in, the body temperature of the user 301, and the distance of the user 301 from the fan to make this determination. Based off this information the computer-based gaming system 209 may determine how long it needs to turn on the fan and at what intensity the fan level should be set to.

The computer-based gaming system 209 may know the game rules and game mechanics of a video game or may identify game rules and game mechanics in real-time. This knowledge may be obtained in various ways, including, but not limited to, preloaded game data, accessing game files, utilizing APIs provided by the game developers, or analyzing gameplay in real-time using machine learning algorithms. For example, the computer-based gaming system 209 may access predefined game rules and mechanics stored in a database or directly from the game files to understand elements such as game objectives, level structures, and difficulty settings. Alternatively, the computer-based gaming system 209 may employ real-time analysis techniques, such as pattern recognition or gameplay monitoring, to identify game mechanics as they occur. Using this information, the computer-based gaming system 209 may apply alterations 309 accordingly, such as implementing a select number of alterations per game loop.

The computer-based gaming system 209 may specify a predetermined maximum number of alterations 309. This predetermined maximum and/or select number may be determined through various methods. The computer-based gaming system 209 may allow the user to set this number and/or may determine it based on factors such as the user's age, health history, and/or gaming habits. The computer-based gaming system 209 may also or instead use machine learning and/or artificial intelligence to determine an appropriate number of alterations 309.

Upon determining an unhealthy condition 307 and/or potentially unhealthy condition, the computer-based gaming system 209 may select a number of alterations 309 such as 10 that may be applied to one or more ways in which the user 301 interacts with the digital media 217. The computer-based gaming system 209 may then alter 309 the computer-based gaming system 209 and deduct an alteration 309 from the select number each time an alteration 309 is applied. The alterations 309 may be used individually and may or may not be applied all at once.

When an alteration 309 is used, the computer-based gaming system 209 may initiate a cooldown period for that specific alteration 309 and/or all alterations 309. For example, when there are 10 alterations 309 and 1 alteration 309 is used, the alteration number may regenerate during the cooldown period; so, when the cooldown period is over, the user 301 may be back at 10 alterations 309. The computer-based gaming system 209 may track the frequency of alteration 309 usage. Going over an alteration usage limit within a select time frame may be used to determine the severity of the user's 301 unhealthy condition 307 and/or potentially unhealthy condition.

The computer-based gaming system 209 may also or instead first apply an alteration 309 upon detecting an unhealthy condition 307, and then select a number of additional alterations 309. The number of alterations 309 may be based on the severity of the unhealthy condition 307 and/or other factors.

Once the predetermined, predefined, and/or select number of alterations 309 is exhausted, the computer-based system 209 may apply a cooldown period in which no further alterations 309 are made to the one or more ways in which the user interacts with the digital media 217 until the cooldown period has elapsed. After and/or during this cooldown period, the computer-based gaming system 209 may regenerate the same number of alterations 309 or generate a different number of alterations 309.

The regeneration analysis for the number of alterations 309 may consider various factors. These various factors may include the severity of the unhealthy condition 307, how often an unhealthy condition 307 in the user 301 occurs during their digital media interaction session, the user's 301 response to previous alterations 309, the frequency of alteration usage, and/or the overall duration of the digital media session.

The computer-based gaming system 209 may continue this cycle of applying alterations 309, exhausting the select number, entering cooldown periods, and regenerating alterations 309 as long as the user 301 continues to interact with the digital media 217 and/or as long as an unhealthy condition 307 are detected.

The computer-based gaming system 209 may include a feature that alters 309 one or more, but not all, aspects of the digital media interaction, while specifically avoiding alterations 309 to features that directly contribute to a win condition.

When the computer-based gaming system 209 detects an unhealthy condition 307 in the user 301, it may analyze the digital media elements to identify which features are critical to achieving a win condition. The computer-based gaming system 209 may then implement alterations 309 that exclude these critical features.

For example, in a competitive game, the computer-based gaming system 209 may alter 309 visual elements, audio cues, or non-essential controls, but may not alter 309 the core mechanics that determine the outcome of the competition. In a wagering game, the computer-based gaming system 209 may adjust the user interface or the pace of play, but may not alter 309 the odds or the core gameplay that determines the wager outcome.

The computer-based gaming system 209 may maintain a database of game features categorized by their impact on win conditions. This database may be updated regularly to ensure accurate identification of critical gameplay elements across various game types.

The computer-based gaming system 209 may have a select time period during which it must receive confirmation that an alteration 309 is being used in response the user's unhealthy condition 307 and/or potentially unhealthy condition. This confirmation can come from either the user 301 or a person(s) monitoring the user's 301 digital media interaction session.

The alteration 309 may remain available while the user 301 continues to interact with the digital media 217, or while the person(s) monitoring the user's 301 digital media interaction session remains connected to the user's 301 computer-based gaming system 209. If the alteration 309 is not utilized within the select time period, it may become unavailable to the user 301 and/or the person(s) monitoring the user's 301 digital media interaction session.

Alternatively, the gaming system may provide alterations 309 in response to unhealthy conditions without imposing any time limit for the alterations to be used.

The user 301 may select which unhealthy condition 307 they want to improve. The computer-based gaming system 209 may allow the user to stack these alterations 309. If the unhealthy condition 307 worsens and the user 301 is not using the alteration 309, the computer-based gaming system 209 may use an alteration automatically 309 that is likely to improve the unhealthy condition 307.

The computer-based gaming system 209 may also be designed to receive user input of a time period in which the computer-based gaming system 209 allows to pass before altering 309 one or more but not all ways in which the user interacts with the digital media 217.

Example: The computer-based gaming system 209 may receive information that the user sets this delayed alteration process to 1 minute. If an unhealthy condition is detected, the computer-based gaming system 209 may wait 1 minute then proceed with altering 309 one or more but not all ways in which the user interacts with the digital media 217.

The computer-based gaming system 209 may implement this delayed alteration 309 feature for various types of unhealthy conditions and/or alterations 309. The delay time may be adjustable by the user and/or determined by the computer-based gaming system 209 based on the severity of the unhealthy condition.

The computer-based gaming system 209 may also or instead provide options for the user to accept, reject, or modify the proposed alteration 309 during the delay period.

The computer-based gaming system 209 may display or auditorily present the alteration number to the user. When an alteration 309 occurs, the computer-based gaming system 209 may subtract an alteration 309 from this number. The computer-based gaming system 209 may issue a warning when a user 301 is on their last alteration 309 or nearing their last alteration 309. The computer-based gaming system 209 may also or instead add an alteration 309 during the user's 301 digital media interaction based on different criteria. These criteria may include improved vital sign(s) 303, extended periods of healthy gameplay, or completion of specific in-game tasks.

The computer-based gaming system 209 may visually or auditorily display to the user 301 what is being altered 309. This may include on-screen notifications, color-coded indicators, or audio cues that inform the user of the specific changes being made to their gameplay experience. The computer-based gaming system 209 may provide options for the user 301 to customize how this information is presented. A user 301 may choose visual, auditory, or haptic feedback for alteration notifications.

The computer-based gaming system 209 may also or instead maintain a log of alterations 309 applied during a digital media interaction session. This log may be accessible to the user 301 and/or to person(s) monitoring the user's 301 digital media interaction session, allowing them to review the history of alterations 309 made.

The computer-based gaming system 209 may use this alteration tracking feature to analyze patterns in the user's health and gameplay over time. This data may inform future alteration 309 decisions and may be used to generate personalized health recommendations for a user 301.

The computer-based gaming system 209 may include a feature where the cooldown period duration may speed up or slow down based on different criteria. The computer-based gaming system 209 may add time to and/or subtract time from the cooldown period duration.

For example, the computer-based gaming system 209 may alter 309 the cooldown period based on the user's 301 unhealthy condition 307 and/or potentially unhealthy condition improving, not improving, or getting worse. Given any of the scenarios, the cooldown period may be reduced or extended.

The computer-based gaming system 209 may use various criteria to determine these cooldown period adjustments. These criteria may include one or more of the following: The rate of change in the user's 301 vital sign information 305, The severity of the unhealthy condition 307 and/or potentially unhealthy condition, The user's 301 overall digital media interaction session duration, The frequency of alteration 309 usage, and the effectiveness of previous alterations 309.

The computer-based gaming system 209 may also or instead allow users to view their current cooldown period status and any adjustments made. This information may be presented visually or auditorily to the user.

The computer-based gaming system 209 may include an unhealthy condition 307 and/or potentially unhealthy condition sensitivity level feature. The level of fluctuating vital sign information 305 may be set by a user 301 and/or operator. This sensitivity level may act as the predefined criteria that triggers an alteration in response to an unhealthy condition.

Example: The unhealthy condition sensitivity level may be set to +1. This may mean, if the user's heartbeat information received by the computer-based gaming system 209 increases by +1, this may trigger the alteration 309 in response to the unhealthy condition. The computer-based gaming system 209 may be set to trigger an alteration 309 in response to an unhealthy condition 307 when the heartbeat rises at least +1.

This may also work vice versa. For example, the unhealthy condition sensitivity level may be set to −1. This may mean, if the user's vital sign information 305 received by the computer-based gaming system 209 decreases by −1, this may trigger the alteration 309 in response to the unhealthy condition 307 and/or potentially unhealthy condition.

The computer-based gaming system may adjust sensitivity levels based on a combination of vital sign information and/or biometric information and/or physiological information and contextual information. For example: If the heart rate increases by +1 (meeting the current sensitivity level threshold of +1), but the computer-based gaming system 209 determines no stress is present, the computer-based gaming system may adjust the new sensitivity level to +2.

The computer-based gaming system 209 may allow for different sensitivity levels for different vital sign(s), and/or different types of digital media content the user 301 interacts with.

The computer-based gaming system 209 may incorporate a dual-level system for initiating alterations 309: a sensitivity level and a trigger level.

The computer-based gaming system 209 may include a feature for adjustment of sensitivity levels throughout the day.

The computer-based gaming system 209 may allow a user 301 to set sensitivity levels for various times of the day. For Example: A user may configure the computer-based gaming system 209 as follows: Sensitivity level +1 during 8 am-4 pm (regular daily activities) Sensitivity level +10 from 5 pm-12 am or until vitals return to the regular range (post-exercise period). The computer-based gaming system 209 may maintain a schedule of these varying sensitivity levels.

The computer-based gaming system 209 may provide an interface for users to view and edit their sensitivity level schedule, potentially integrating visual representations of how these levels change throughout the day.

The computer-based gaming system 209 may incorporate an additional feature to the sensitivity level functionality:

If the user's vital sign(s) 303 return to a range that is below the current sensitivity level, and an alteration 309 was previously made available due to the sensitivity level being above and/or below a certain threshold, the computer-based gaming system 209 may: Make the alteration 309 no longer available for use; If the alteration 309 is currently in use, the computer-based gaming system 209 may stop or gradually phase out the alteration 309. The computer-based gaming system 209 may update any user interfaces to reflect the changed availability of alterations 309.

The computer-based gaming system 209 may automatically determine and set sensitivity levels based on historical or present user vital sign information 305.

Third-Party Set Sensitivity: The computer-based gaming system 209 may allow authorized third parties (e.g., healthcare providers, parents, or designated monitors) to set or adjust sensitivity levels remotely. This may be particularly useful in therapeutic or supervised gaming contexts.

Additional Features

The computer-based gaming system 209 may allow for hierarchical control, where settings by one party may override others (e.g., monitor settings superseding user settings).

The computer-based gaming system 209 may provide options for temporary overrides or time-limited sensitivity level adjustments.

The computer-based gaming system 209 may implement a notification system to alert users or monitors of sensitivity level changes.

The computer-based gaming system 209 may record a log of sensitivity level changes, including who made the changes and when.

The computer-based gaming system 209 may offer preset sensitivity profiles for different scenarios (e.g., casual gaming, competitive play, health management, web surfing).

The computer-based gaming system 209 may include a feature that allows users and/or the computer-based gaming system 209 to save alterations. These saved alterations may be applied for next use or continued use. A user 301 may be able to turn these applied alterations 309 off and/or on and/or on standby. The computer-based gaming system 209 may also or instead be able to turn them off or on based on the user's 301 health condition.

The computer-based gaming system 209 may store these saved alterations on the storage media 211 and/or the host system 201. These stored alterations 309 may be accessed and/or used by other users or person(s) who monitor a user's 301 digital media interaction sessions.

Alterations 309 may be saved and/or downloaded to be bundled together to create an alteration 309 package. An alteration 309 package may be a collection of one or more alterations 309 grouped together that may be used by a user 301 and/or assigned to a user 301 by the computer-based gaming system 209 and/or other users/person(s) who monitor the user's digital media 217 interaction session in a manner to improve and/or prevent an unhealthy condition 307 while a user 301 interacts with digital media 217. The number of alterations 309 set to work in conjunction with a computer-based gaming system may be limited to a predetermined number. The number of alteration 309 packages may be limited to a predetermined number also.

Alterations 309 and/or alteration 309 packages may come pre-installed and available for immediate implementation and use on the computer-based gaming system 209. Additionally, there may be alterations 309 and/or alteration 309 packages available for download, installation, implementation, and use from online digital media repositories or stores. These pre-existing or downloadable alterations 309 and/or alteration 309 packages may be designed to address a common unhealthy condition 307, prevent an unhealthy condition 307, optimize digital media interaction experiences, or cater to specific user 301 preferences and/or needs. The computer-based gaming system 209 may automatically suggest or apply these pre-installed or downloadable alterations 309 and/or alteration packages 315 based on detected unhealthy conditions 307, user 301 behavior patterns, or game-specific requirements. User's 301 and/or person(s) who monitor a user's 301 digital media 217 interaction sessions may also have the option to browse, select, and customize these pre-existing alterations 309 and/or alteration 309 packages to suit the user's 301 needs and/or preferences.

Alterations 309 and/or alteration packages 309 and/or unhealthy conditions 307 may be transferred, downloaded, or assigned to various storage devices, such as USB drives, CDs, ROMs, SD cards, or other external storage media. These alterations 309 and/or alteration packages 309 may also be used in conjunction with digital media interaction sessions on systems with physical media capabilities. For example, if a user 301 is interacting with digital media 217 on a computer-based gaming system 209 that can receive physical storage media (e.g., a disc drive, ROM slot, or SD card slot), a disc, ROM cartridge, or SD card containing alterations 309 and/or alteration packages 309 may be inserted to operate alongside the user's 301 digital media interaction.

When a user's 301 vital sign information 305 is received by the computer-based gaming system 209, and it determines that the vital sign information indicates an unhealthy condition 307, the computer-based gaming system's 209, with a processor, may alter 309 the user's 301 interaction with the digital media in one or more ways to improve the unhealthy condition 307 while the user 301 continues to interact with the digital media 217. These alterations 309 may be applied using information from the storage device alone or in combination with other sources, such as online communications. For instance, if a user 301 is playing a first-person shooter game and the system detects an unhealthy condition 307, such as increased heart rate indicative of anxiety, the computer-based gaming system 209 may use alterations 309 stored on an inserted SD card to alter the video game's environment. This may involve reducing the intensity of the game, such as dimming the visual effects, lowering the sound volume, or even altering the appearance of in-game enemies to make them less frightening. Additionally, the system may further enhance this alteration by downloading additional calming audio tracks from an online source, ensuring that the user's interaction with the digital media 217 is adjusted in real-time to improve the detected unhealthy condition 307.

Alternatively, a user 301 who prefers digital downloads may also or instead download alterations 309 and/or alteration 309 packages to the computer-based gaming system 209 for use during digital media 217 interactions. A user may able to download alterations 309 and/or alteration 309 packages directly on to a video game. A user 301 may also be able to have different alterations and/or alteration packages for different digital media. for example, a user 301 may have an alteration that reduces speed of the gameplay for a rhythm game, an alteration that provides in game directions in a role-playing game, and an alteration that get's rid of gore scenes from a video game or movie.

The computer-based gaming system 209 may allow a user 301 and/or person(s) who monitor the user's 301 digital media 217 interaction sessions to create one or more packages of saved alterations 309.

The computer-based gaming system 209 may provide an interface for users to manage their saved alterations 309. This may include options to edit, delete, or create new alteration packages.

For example, if the user 301 has an unhealthy condition 307 where they experience heat flashes, and a stressful scenario is causing the heat flash by the one or more ways in which the user 301 interacts with the digital media 217. A user 301 may have a saved alteration to where the computer-based gaming system 209 improves the unhealthy condition 307 by turning on the air conditioner to a select temperature the user 301 has saved.

The computer-based gaming system 209 may receive information indicating that the user is no longer experiencing and/or has an improved unhealthy condition 307 and/or potentially unhealthy condition, such as stress and/or elevated body temperature, when an alteration 309 such as activating an air conditioner and/or fan, is implemented to improve the unhealthy condition and/or potentially unhealthy condition 307. This received information may include: The duration of the alteration 309 (e.g., how long the fan and/or air conditioner was on), The intensity of the alteration 309 (e.g., what setting/temperature the fan and/or air conditioner was set to), and the time it took for the user's unhealthy and/or potentially unhealthy condition to improve and/or no longer be experienced by the user. This information may be used for alteration 309 parameters and/or strategies by the computer-based gaming system 209.

The computer-based gaming system 209 may save all or part of this information. When the user 301 experiences the same unhealthy condition during future interactions with the digital media 217 using the computer-based gaming system 209, it may use all or part of this saved information to improve the unhealthy condition 307 in a timely manner tailored to that specific user 301. The computer-based gaming system 209 may update and refine this information over time. The alteration 309 parameters and/or strategies of the computer-based gaming system 209 may be subject to change based on this accumulated data and ongoing user experiences. The computer-based gaming system 209 may also or instead use machine learning and/or artificial intelligence to analyze this data and optimize its responses to unhealthy conditions across different users and scenarios. This saved information may be stored on any of the components shown in FIG. 2. It may also be saved externally such as a USB (universal serial bus) stick, CD (compact disc) etc., that the user may use in conjunction with the computer-based gaming system 209.

The computer-based gaming systems 209 saved alterations 309 and/or alterations 309 parameters and/or strategies may work per user profile. Example, consider a household where there is one computer-based gaming system 209 and more than one user that uses the computer-based gaming system 209. Each user may be able to create their own user profile and these alteration 309 settings are stored for each user. The computer-based gaming system 209 may also or instead use user identifiers such as, facial recognition, finger print detection, voice recognition. Example, say the computer-based gaming system 209 has one user profile, all household users of the computer-based gaming system 209 may use this one profile and once they use one of the unique identifiers, their saved alterations 309 may be in effect and the computer-based gaming system 209 alterations 309 will be for that user. This may also work with two users playing together locally. For example, two users playing locally may each have their own alterations 309.

When a user 301 starts a digital media interaction session, the computer-based gaming system 209 may prompt the user 301 to select from their saved alteration packages or to start with default settings.

The computer-based gaming system 209 may also or instead use machine learning and/or artificial intelligence to suggest optimal alteration 309 packages based on the user's historical data and current health status.

If the computer-based gaming system 209 detects a significant change in the user's 301 vital sign information 305 during gameplay, it may automatically switch to a more appropriate saved alteration package, if available.

The computer-based gaming system may allow a user 301 to share their alteration 309 packages with another user 301.

The computer-based gaming system 209 may generate reports on the effectiveness of different alteration packages, helping a user 301 and/or the computer-based gaming system 209 to refine and optimize these settings over time.

Here are some examples on how these features may be executed:

Saving and Applying Alterations:

Example: A user 301 experiences eye strain during long gaming sessions. The computer-based gaming system 209 alters 309 the screen brightness and color temperature. The user 301 finds this helpful and saves these alterations 309. In future sessions, these saved alterations 309 may be automatically applied after a set period of digital media interaction or at the start of digital media interaction or at the start of certain digital media interaction such as playing a specific video game.

Turning Alterations on/off:

Example: A user 301 has saved alterations that reduce game speed when their heart rate elevates. They may choose to turn this alteration 309 off for a competitive match, but keep it on for casual play. The computer-based gaming system 209 may also turn this alteration 309 on automatically if it its deemed necessary.

Multiple Alteration Packages:

Example: A user 301 creates three alteration 309 packages: one for action games that adjusts control sensitivity when stress levels rise, one for strategy games that provides more frequent breaks when concentration wavers, and one for late-night digital media interaction which may include web surfing, watching videos, and/or gaming that gradually reduces screen brightness.

Managing Saved Alterations:

Example: Through an in-game menu, a user may view their saved alteration packages, edit the heart rate threshold that triggers a game speed reduction, delete an outdated set, or create a new set for a recently purchased game.

Selecting Alterations 309 at Session Start:

Example: When launching a game, the user may be prompted: "Would you like to use your 'Late Night Gaming' alteration 309 package, your 'Action Game' package, or start with default settings?"

AI-Suggested Alterations:

Example: Based on data showing the user 301 often takes breaks during long puzzle sequences, the computer-based gaming system 209 may suggest and/or implement new alteration package(s) that automatically pauses the video game and suggests a short break during extended puzzle-solving sessions. The computer-based gaming system 209 may create these package(s) on its own and/or use alteration package(s) other user(s) created. It may also create its own alterations based on other user(s) created alteration packages.

Automatic Switching of Alteration 309 Packages:

Example: If the computer-based gaming system 209 detects rapid eye movement and increased heart rate during a horror game, it may switch from the user's 301 standard alteration package to one designed to reduce stress, perhaps by slightly brightening dark scenes or lowering sudden sound effects.

Sharing Alteration Packages:

Example: A user 301 who has created an effective alteration package for managing hand strain in fighting games may share this set with friends, who can then implement and use it in their own digital media interaction sessions.

Effectiveness Reports:

Example: The computer-based gaming system 209 may generate a monthly report showing that when using the 'Action Game' alteration package, the user's 301 average heart rate during gameplay decreased by 10%, and their play sessions lasted 20% longer before taking breaks.

The computer-based gaming system 209 may include a feature that may be triggered automatically and/or may prompt the user 301 when it wants to make an alteration 309 to one or more ways in which the user 301 interacts with the digital media 217. The prompt may ask if the user 301 wishes to proceed with the alteration 309 or not.

A user 301 may be able to have the alteration 309 only occur for specific vital sign(s) and/or vital sign information 305 and/or unhealthy condition(s). For example, the computer-based gaming system 209 may be set to trigger an alteration 309 automatically and/or trigger a prompt to the user 301 that it wants to alter 309 one or more ways in which the user 301 interacts with the computer-based gaming system 209 only when at least one specified vital sign of a user 301 is indicative of an unhealthy 307 and/or potentially unhealthy condition. The computer-based gaming system 209 may set this itself if it notices a pattern by the user 301 that only at least one specified vital sign 303 are indicative of an unhealthy condition 307 and/or potentially unhealthy condition.

If the computer-based gaming system 209 detects an unhealthy condition 307 in a user's 301 or respiratory rate but the computer-based gaming system 209 is set to only detect an unhealthy condition 307 in the user's 301 heartbeat and/or set to only apply alterations 309 to an unhealthy condition 307 in the user's 301 heartbeat of, the computer-based gaming system 209 may let the user know of this unhealthy condition 307 finding and ask them if they want to turn on alterations 309 for user's 301 respiratory rate. The computer-based gaming system 209 may also let the user 301 know if they want to set respiratory rate as a unhealthy condition 307 that is detected by the computer-based gaming system 209. The computer-based gaming system 209 may implement alteration 309 packages in this instance in a manner to improve the unhealthy condition 307. The alteration 309 packages may be created by the computer-based gaming system 209 in Realtime and/or the user 301 in real-time when the unhealthy condition 307 and/or potentially unhealthy condition is detected. The computer-based gaming system 209 and/or user 301 may also use alteration packages created by other users.

The computer-based gaming system 209 may be set to alter 309 nothing automatically in response to an unhealthy condition 307 in any vital sign 303 that is detected. It may be designed to where once it does detect an unhealthy condition 307, it prompts the user whether visually, auditorily, or through haptic feedback of the unhealthy condition 307 and how an alteration is available to use in response to the detected unhealthy condition 307 and/or potentially unhealthy condition. The user 301 may choose to allow alterations 309 or not.

The computer-based gaming system 209 may allow a user 301 to choose what is altered 309 beforehand. For example, a user 301 may set the computer-based gaming system 209 so that only audio and haptic feedback from an input peripheral 205 is altered 309 when an unhealthy condition 307 is detected.

The computer-based gaming system 209 may provide a menu or interface where users can select which elements of the digital media 217 and/or components working in conjunction with the computer-based gaming system 209 may be altered 309 in response to a detected unhealthy condition 307. This menu elements may include, but may not be limited to, visual effects, audio, haptic feedback, game difficulty, or input sensitivity.

The computer-based gaming system 209 may allow a user 301 to set different alteration preferences for different types of digital media content, different times of day, or different detected unhealthy condition(s) 307 and/or potentially unhealthy conditions.

The computer-based gaming system 209 may implement alterations 309 that last for a predetermined, predefined, or select time period. The duration of these alterations 309 may also be contingent on the user's 301 vital sign information 305 improving.

For instance, consider a scenario where the computer-based gaming system 209 detects an unhealthy condition 307 such as elevated heart rate in a user 301 playing a first-person shooter game. In response to the unhealthy condition 307, the computer-based gaming system 209 implements an alteration 309 that reduces the game's difficulty level and lowers the intensity of visual effects. This alteration 309 is initially set to last for a predetermined time period of 15 minutes.

However, the computer-based gaming system 209 continues to monitor the user's 301 vital sign information 305 during this period. If after 10 minutes, the computer-based gaming system 209 detects that the user's 301 vital sign information 305 has returned to a normal range, it may automatically end the alteration 309 earlier than the predetermined 15-minute duration.

Conversely, if after the initial 15-minute period, the user's 301 vital sign information 305 remains elevated indicative of an unhealthy condition 307, the computer-based gaming system 209 may extend the duration of the alteration 309. This extension may continue until the vital sign information 305 shows improvement, such as the heart rate returning to a healthy range.

In another scenario, the computer-based gaming system 209 may implement an alteration 309 that gradually increases the game's brightness over time to combat the user's 301 fatigue. This alteration 309 may be set to continue until the user's 301 eye movement patterns and reaction times, as part of their vital sign information 305, indicate improved alertness.

If the alteration 309 duration is set to a fixed time period, the computer-based gaming system 209 may still monitor the user's 301 vital sign information 305 during this period. If the unhealthy condition 307 persists and/or worsens, the computer-based gaming system 209 may extend the alteration period or implement additional alterations 309.

The computer-based gaming system 209 may provide a user 301 with real-time feedback on their vital sign information 305 and the remaining duration of active alterations 309. This information may be displayed visually or conveyed through audio cues, or through haptic feedback mechanisms.

The computer-based gaming system 209 may incorporate an audio sensitivity feature combined with geolocation of the user 301 to determine and adjust audio levels. The computer-based gaming system 209 may use geolocation technology to identify the user's 301 location and potential living environment.

The computer-based gaming system 209 may monitor the user's audio input levels through microphones integrated into or connected to the computer-based gaming system 209. For Example, the computer-based gaming system 209 detects that the user's 301 voice or other audio input is loud, and the geolocation data indicates they live in an apartment, the computer-based gaming system 209 may recommend that the user 301 quiets down.

The computer-based gaming system 209 may also or instead automatically adjust its audio output levels based on this information. For instance, it may lower speaker output to prevent disturbance to potential neighbors in close living quarters. The computer-based gaming system 209 may allow a user 301 to set different audio sensitivity profiles for different times of day or different days of the week.

The computer-based gaming system 209 may also provide visual or audio cues to the user 301 when audio levels exceed a threshold based on their geolocation. The computer-based gaming system 209 may also or instead incorporate this feature into multiplayer games, adjusting an individual user's 301 audio outputs and/or input levels.

The computer-based gaming system 209 may allow a user 301 to override these audio adjustments, but may provide warnings about potential noise disturbances if the user chooses to do so.

The computer-based gaming system 209 may include a feature where a cooldown period is lifted if the user's 301 vital sign information 305 return to a healthy state. The computer-based gaming system 209 may set a cooldown period after alterations 309 are applied or exhausted. However, if the user's 301 vital sign information 305 return to a healthy condition before the cooldown period is over, the computer-based gaming system 209 may lift the cooldown period. For example, if a 10-minute cooldown period is set, but the user's vital sign information 305 return to healthy levels after 5 minutes, the computer-based gaming system 209 may end the cooldown period at that 5-minute mark. The computer-based gaming system 209 may continuously monitor the user's 301 vital sign information 305 during the cooldown period to determine if they have returned to a healthy state.

The computer-based gaming system 209 may provide visual or audio cues to inform the user when the cooldown period has been lifted due to improved vital sign information 305. The computer-based gaming system 209 may also or instead use this early cooldown lifting as positive reinforcement, potentially rewarding the user with additional alterations 309 or other in-game benefits.

Figure 12:
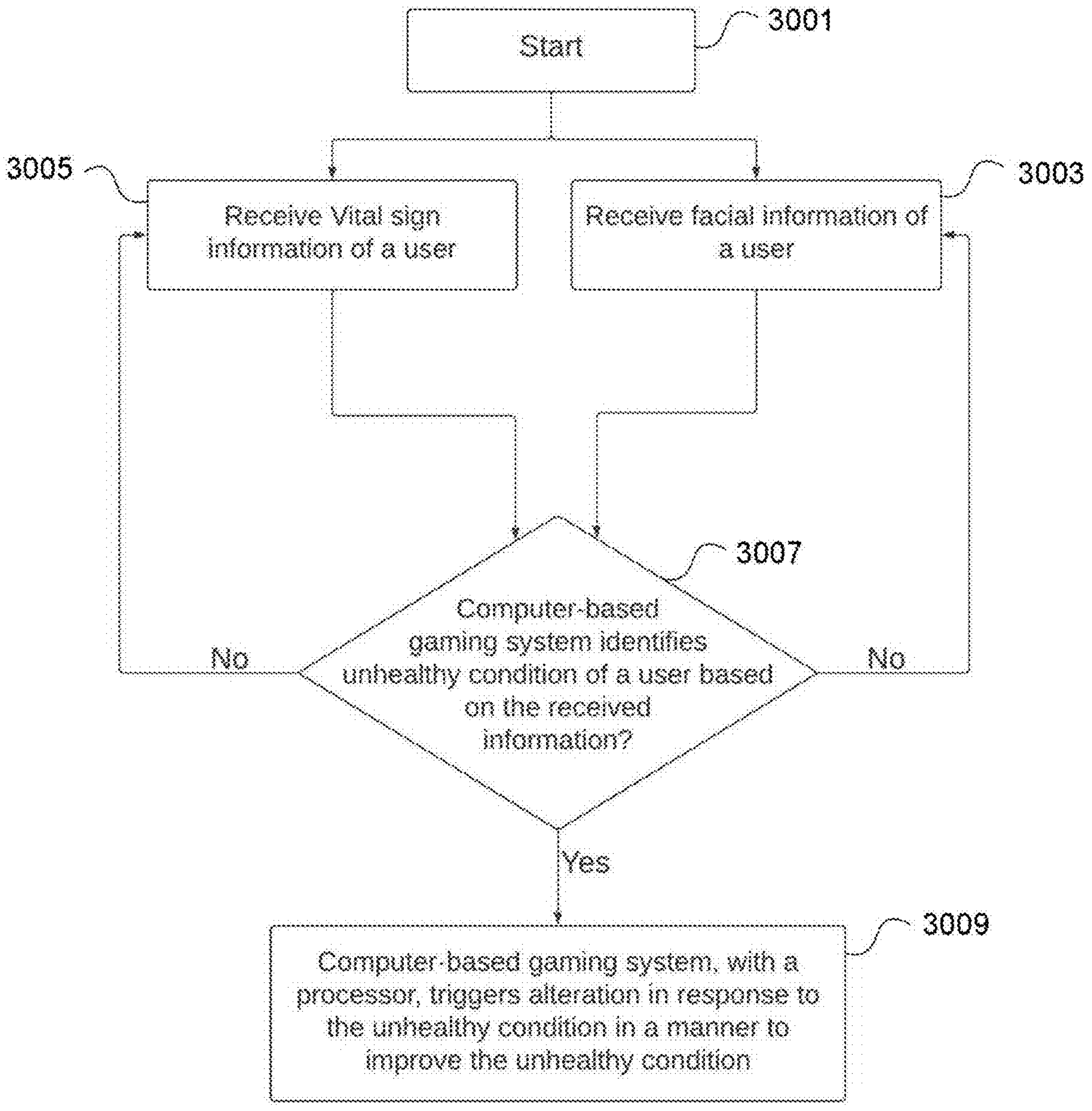
FIG. 12 illustrates a flow chart of an example of a process of a computer-based gaming system.
Figure 13:
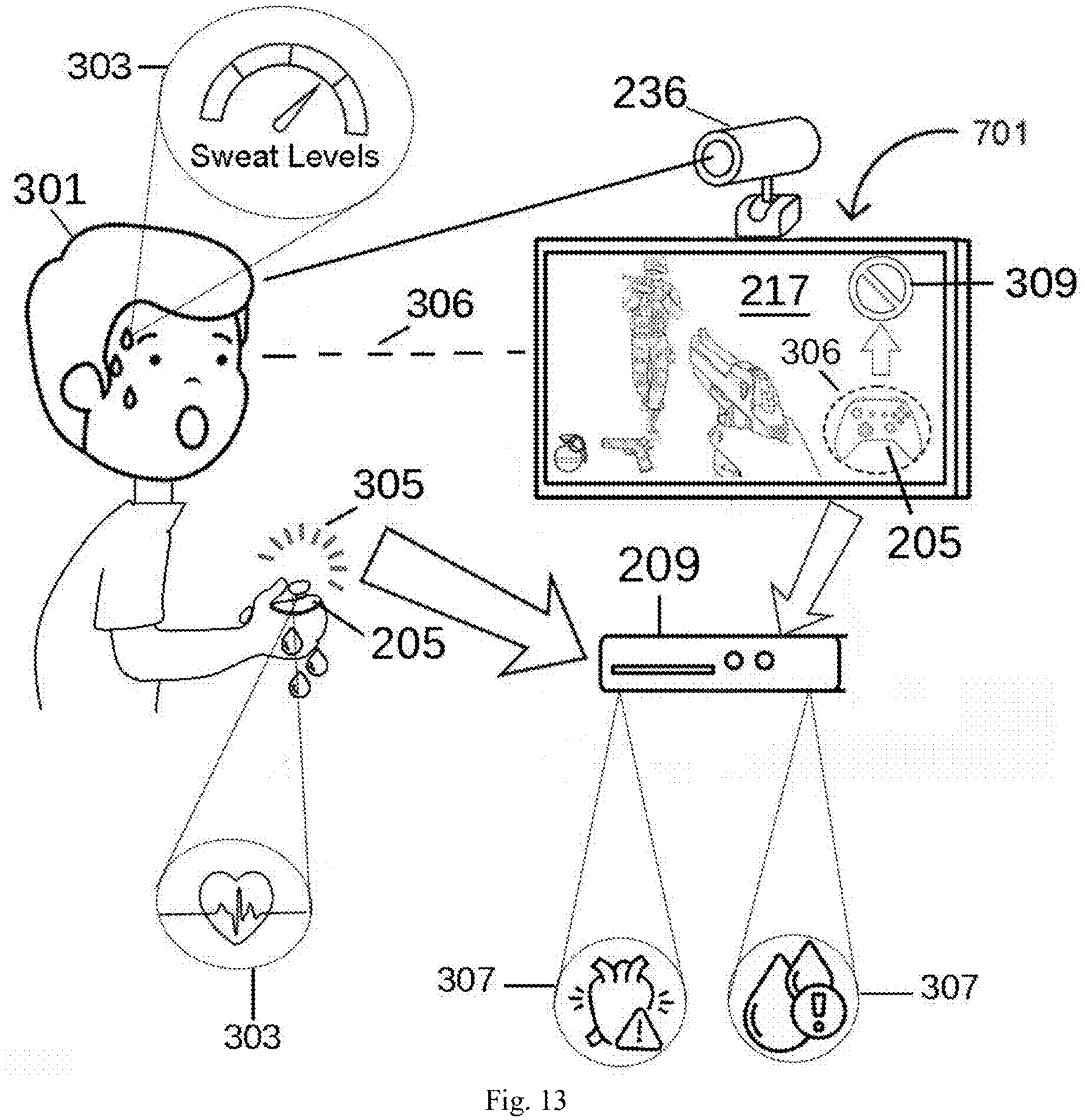
FIG. 13 is an example of a computer based-gaming system altering functionalities in one or more ways in which the user interacts with the digital media in response to a user's unhealthy condition.

Eye tracking feature with practical examples that may be used with FIG. 12 and/or FIG. 13: The computer-based gaming system 209 may utilize eye tracking to determine an unhealthy condition 307 in a user 301 to alter 309 the user's 301 interaction with digital media 217 in a manner to improve the unhealthy condition 307. The eye tracking functionality may work in conjunction with another vital sign 303 of the user 301 to determine an unhealthy condition 307 and/or potentially unhealthy condition. Based on this determination, the computer-based gaming system 209 may alter 309 the user's 301 interaction with the digital media 217 in a manner to improve the unhealthy condition 307 of the user 301. The computer-based gaming system 209 may make this determination by receiving, analyzing and/or processing the received eye tracking data in conjunction with a vital sign 303 of the user 301 such as heartbeat information.

The computer-based gaming system 209 may be configured detect a variety of eye tracking patterns such as: sustained user 301 focus on one or more digital media elements for select time periods; the frequency with which a user 301 looks to and from digital media elements within a select period; the count of the number of times a user's eye tracking data focuses on specific digital media 217 elements within a select period. These digital media 217 elements may be elements that are predefined, predetermined, or selected by the computer-based gaming system 209, and/or the user, and/or components that work in conjunction with the computer-based gaming system 209 that may be altered 309. For example, the computer-based gaming system 209 may receive eye tracking data of digital media elements appearing on the digital media display device of one or more 3D clown models in conjunction with fluctuating heartbeat information of the user 301.

The computer-based gaming system 209 may then alter 309 the digital media elements in a manner to improve the unhealthy condition 307. This may also be done by replacing and/or swapping the digital media 217 elements with predetermined, predefined, or select digital media elements. For example, when the clowns are 3D models in a video game, the computer-based gaming system 209 may be designed so when an unhealthy condition 307 is detected by a user 301 that may be caused by the 3D models, the 3D model may be blurred out. The 3D model may also or instead be replaced and/or swapped by a 3D model the computer-based gaming system 209 determines may improve the unhealthy condition 307.

The eye tracking functionality may operate within select alterable 309 areas, predetermined alterable 309 areas, and/or predefined alterable 309 areas of the digital media 217 rather than freely across the entire digital media 217. For example, in a war simulation video game, the digital media 217 may include a display to the user 301 consisting of various digital media 217 elements that may be positioned in certain locations such as: Game world elements such as a soldier character positioned in the center of the digital media 217, a virtual environment such as a jungle surrounding the soldier character; User interface (UI) elements such as a health bar which may be positioned in the bottom right of the digital media 217, equipped weapon display indicative of what weapon(s) the soldier character is using in the war simulation video game such as an AK-47 and/or lethal equipment such as grenades positioned in the bottom left of the digital media 217; and navigation aids such as mini-map which may be positioned in the top right of the digital media 217 that may be indicative of the soldier characters position in the virtual environment of the jungle. The computer-based gaming system 209 may determine, based on received eye tracking data and vital sign information 305 such as the user's 301 heartbeat, that the user 301 may want to alter 309 one or more of these digital media elements. For example, the computer-based gaming system 209 receives eye tracking data from the user 301 in conjunction with vital sign information 305 of indicative of an unhealthy condition 307 of the user 301 such as an elevated heartbeat. The received eye tracking information is located on the position of at least one of these select digital media 217 elements such as the lethal equipment located on the bottom left of the digital media 217. The computer-based gaming system 209 may determine, based on this received information to trigger an alteration 309 to the select, predetermined, and/or predefine digital media 217 element(s) in a manner to improve the unhealthy condition 307. This alteration 309 may cause by regeneration of the amount of lethal equipment or changing the lethal equipment to something more suitable for the specific gaming situation for example.

The computer-based gaming system 209 may display a visual indicator of the user's 301 input peripheral 205 on the digital media 217. The computer-based gaming system 209 may receive eye tracking data focused on this visual indicator. In scenarios where the user 301 may be engaged in intense gameplay, the input peripheral 205 may be equipped to detect physiological responses such as excessive hand sweat. When the input peripheral 205 and/or the computer-based gaming system 209 detect this condition, they may determine it as an unhealthy condition 307 and/or potentially unhealthy condition. To avoid disrupting the user's 301 focus during critical gameplay moments, the computer-based gaming system 209 may not immediately activate corrective measures. Instead, if the computer-based gaming system 209 receives information that the user 301 has been looking at the input peripheral's visual indicator on the digital media 217 for a select time period and/or for a select number of times within a select time period. while the unhealthy condition 307 and/or potentially unhealthy condition is detected, the computer-based gaming system 209 may then trigger an alteration 309.

The alteration 309 may involve the computer-based gaming system 209 and/or the input peripheral 205 activating a cooling mechanism, such as a fan located in the input peripheral 205. This activation may aim to improve the unhealthy condition 307 and/or potentially unhealthy condition. The cooling mechanism may operate for a select time period, or until the input peripheral 205 determines the detected physiological response has returned to a healthy range. This process may also be triggered when the computer-based gaming system 209 detects the user looking at the physical input peripheral 205 itself, employing the same decision-making process and response. The physical input peripheral 205 may be designed to received eye tracking information.

The computer-based gaming system 209 may also be designed so a menu appears in response to the unhealthy condition 307 and/or potentially unhealthy condition that may consist of alteration settings for the digital media 217. The user 301 may customize these settings to their personal liking. For example, the user 301 may make this selection and/or during the digital media interaction session, when an unhealthy condition 307 occurs, the user 301 is prompted with an array of digital media elements and may select which digital media element(s) they want to alter 309 the digital media element(s) that is contributing and/or are causing the unhealthy condition 307 and/or potentially unhealthy condition 307 within the user's 301 interaction with digital media elements.

The computer-based gaming system 209 may also have access to the internet and search the symptoms in real time and determine if the user 301 is experiencing symptoms of an unhealthy condition 307 and/or potentially unhealthy condition or is experiencing an unhealthy condition 307 and/or potentially unhealthy condition. The eye tracking functionality may be designed to operate freely and/or within select areas and/or select alterable areas of the digital media 217. An example of how the eye tracking functionality may operate given select areas is, in scenarios where multiple alterable digital media 217 elements are in close proximity, the computer-based gaming system 209 may employ a mapping algorithm to associate eye tracking data with the nearest alterable digital media element.

The computer-based gaming system 209 may also display visual indicators representing the tracked areas. These indicators, which may take various forms such as shapes or lines, can appear when the user's 301 focus is detected on an alterable digital media element. The computer-based system 209 may offer configuration options that allow individuals to specify which elements can be altered 309 based on eye tracking data and/or vital sign 303. Based on the collected and interpreted eye tracking data, the computer-based gaming system 209 may trigger alterations 309 to one or more, but not all, ways in which the user 301 interacts with the digital media 217. These alterations 309, designed to improve the user's 301 health, unhealthy condition 307 and/or potentially unhealthy condition may persist for predetermined, predefined, or select durations as appropriate to the specific context and user 301 needs.

The computer-based gaming system 209 may also or instead incorporate eye-tracking technology to allow a user 301 to directly and/or indirectly indicate which digital media elements and/or components working in conjunction with the computer-based gaming system 209 may be altered 309. This indication may be based on various eye movement patterns, including but not limited to, the user 301 focusing on a digital media element for a select amount of time, frequent gaze shifts to a particular element, or specific gaze patterns defined by the computer-based gaming system 209.

For example, the computer-based gaming system 209 may detect that a user 301 is directly and/or indirectly directing their visual attention to digital media 217 content a select duration and/or a frequency of times within a select duration. The computer-based gaming system 209 may interpret this received information as the user's 301 selection for an alteration 309 in response to an unhealthy condition 307.

The computer-based gaming system 209 may include a feature where a select number of alterations 309 may be reached before applying a cooldown period. During this cooldown period, no alterations 309 may be made until after the cooldown period ends.

The computer-based gaming system 209 may set a predetermined number of alterations 309 that can be applied before initiating a cooldown period. This number may be fixed or may vary based on user settings, game type, or other factors. For example, the computer-based gaming system 209 may allow 5 alterations 309 before initiating a cooldown period. Once the 5th alteration 309 is applied, the cooldown period may begin. During the cooldown period, the computer-based gaming system 209 may not make any further alterations 309 in response to a unhealthy condition 307 and/or potentially unhealthy condition until after the cooldown period has elapsed. The cooldown period may take effect immediately after the alteration 309 was successfully completed or within a predefined, predetermined or select time period. For example, say the user 301 is experiencing stress and/or elevated body temperatures. The computer-based gaming system 209 may turn on a fan that is working in conjunction with one or more of the components depicted in FIG. 2 of this document to alleviate the stress and/or elevated body temperature. Once the fan is successfully activated, the cooldown period may immediately be applied and no further alterations 309 are made to the one or more ways in which the user interacts with the digital media 217. Take the same example but this time, the fan is on for 30 seconds and during this 30 second duration period, other alterations 309 may be made within this 30 second duration period, and when the 30 seconds have elapsed, the fan may turn off then cooldown period is applied in which no further alterations 309 may be applied until after the cooldown period has elapsed. All other alterations that may have been made before or during this duration period may also be terminated when the duration period is ends and may be subject to a cooldown period.

The computer-based gaming system 209 may display a countdown timer or other visual indicator to show the user how much time remains in the cooldown period.

The computer-based gaming system 209 may allow a user 301 to set the duration of the cooldown period and/or the number of alterations 309 allowed before the cooldown period begins.

The computer-based gaming system 209 may also or instead use machine learning and/or artificial intelligence to alter these parameters based on the user's 301 vital sign information 305 patterns and gameplay behavior.

After the cooldown period ends, the computer-based gaming system 209 may reset the alteration 309 count and resume normal monitoring and alteration 309 processes.

The computer-based gaming system 209 may provide options for emergency overrides in case of severe health conditions detected during the cooldown period.

The computer-based gaming system 209 may include a feature where there is a select maximum number of alterations 309. When the computer-based gaming system makes an alteration 309 in response to an unhealthy condition, it may place cooldown periods between this maximum number of alterations 309.

The computer-based gaming system 209 may set a predetermined maximum number of alterations 309 that can be applied within a given digital media interaction session or time period.

After each alteration 309, the computer-based gaming system 209 may initiate a cooldown period. During this cooldown period, the computer-based gaming system 209 may continue to monitor the user's vital sign(s) 303 but may not apply further alterations 309.

Once the cooldown period elapses, if an unhealthy condition 307 is detected, the computer-based gaming system 209 may apply another alteration 309 and initiate another cooldown period.

This process may continue until the maximum number of alterations 309 is reached. For example, if the maximum is set to 5 alterations 309, the sequence may be: alteration 309, cooldown, alteration 309, cooldown, alteration 309, cooldown, alteration 309, cooldown, alteration 309.

Once the maximum number of alterations 309 is reached, the computer-based gaming system 209 may make no further alterations 309 until after a final, potentially longer, cooldown period has elapsed.

The computer-based gaming system 209 may allow users to customize the maximum number of alterations 309, the duration of cooldown periods, and the duration of the final cooldown period.

The computer-based gaming system 209 may provide visual or auditory indicators to inform the user of their current alteration 309 count, ongoing cooldown periods, and when the maximum number of alterations 309 has been reached.

The computer-based gaming system 209 may also or instead include an emergency override feature for severe health conditions detected after the maximum number of alterations 309 has been reached.

The computer-based gaming system 209 may apply a cooldown period to the monitoring of at least one vital sign 303 and/or the application of alterations 309.

When a cooldown period is applied after an alteration 309, the computer-based gaming system 209 may also set vital sign monitoring to occur periodically rather than constantly. This periodic monitoring may occur for the same duration as the cooldown period or for a different select amount of time.

The computer-based gaming system 209 may also or instead completely suspend vital sign monitoring for the duration of the cooldown period.

For example, if a 5-minute cooldown period is initiated after an alteration 309, the computer-based gaming system 209 may: Cease all vital sign monitoring for 5 minutes, or, switch to periodic monitoring (e.g., checking vital sign(s) 303 every 30 seconds) for 5 minutes, or Switch to periodic monitoring for a different duration (e.g., 3 minutes of periodic monitoring followed by a return to constant monitoring).

The computer-based gaming system 209 may allow a user 301 to customize these settings, choosing whether to apply cooldown periods to alterations 309 only, vital sign 303 monitoring only, or both.

A user 301 may also be able to set different durations for alteration 309 cooldowns and monitoring cooldowns through the computer-based gaming system 209.

The computer-based gaming system 209 may provide visual or auditory indicators to inform the user when monitoring is active, paused, or operating in a periodic mode.

The computer-based gaming system 209 may include an emergency override feature to resume constant monitoring if certain threshold conditions are met, even during a cooldown period.

Figure 14:
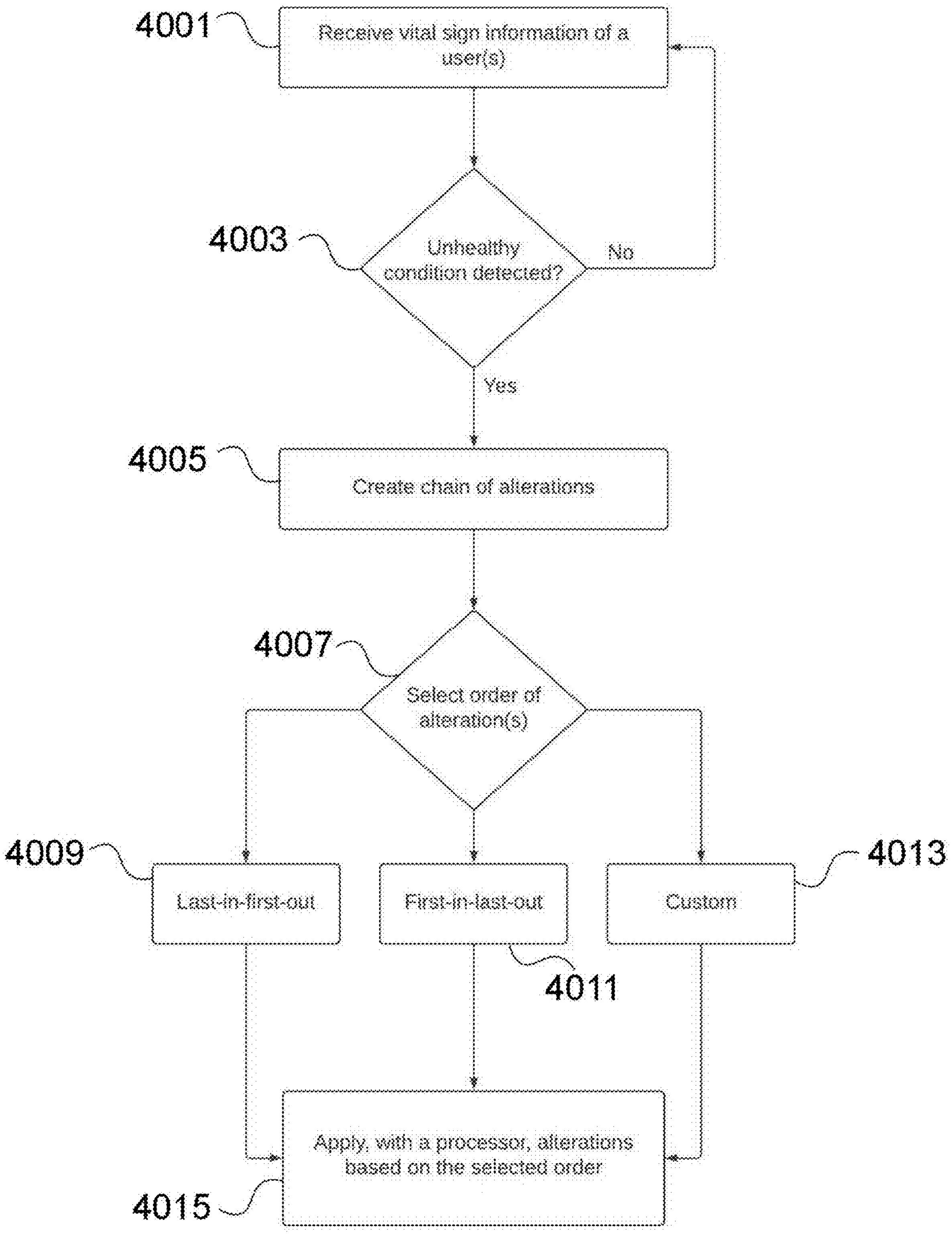
FIG. 14 illustrates a flow chart of an example of a process of a computer-based gaming system.

Chain link feature with practical examples that FIG. 14 may utilize:

The computer-based gaming system 209 may implement a chain link feature for applying alterations 309 in response to detected unhealthy conditions.

The computer-based gaming system 209 may include a feature to identify and implement a chain link of alterations 309, which may be followed by a cooldown period. A cooldown period may be implemented after each chain link resolves or after all chain links have resolved. This chain of alterations 309 may be defined as at least two alterations 309 being applied to at least one user 301 or across multiple users. The cooldown period may apply after each alteration or after all alterations have been applied.

When the computer-based gaming system 209 detects unhealthy conditions in one or more users within a select time period, it may create a chain of corresponding alterations. These alterations may be applied in various orders, such as last-in-first-out, first-in-first-out, or a custom order determined by the system.

When a user has an unhealthy condition and another user has an unhealthy condition within a select time period, this may constitute a chain. The first user who had the first unhealthy condition may be chain link 1, and the second user who experienced the second unhealthy condition may be chain link 2. The order in which alterations are applied in a manner to improve the unhealthy condition 307 of each user to resolve the chain links may vary. For example, chain link 2 may be resolved before chain link 1 or chain link 1 may be resolved before chain link 2. The order in which the chain links resolve may be predetermined or the computer-based gaming system may adjust the resolution order freely. These chain of alterations 309 may be resolved in various orders:

Last In, First Out (LIFO): The most recently added alteration 309 may be resolved first, followed by earlier alterations 309.

First In, First Out (FIFO): Alterations 309 may be resolved in the order they were added to the chain, with the earliest alteration 309 being implemented first.

Last In, Last Out (LILO): The earliest added alteration may be resolved first, with the most recent alteration 309 being implemented last.

Select Order: The computer-based gaming system 209 may determine a custom order for resolving alterations 309 based on various factors such as:

Severity of a user's 301 unhealthy condition 307 compared to another user's 301 unhealthy condition 307.

The computer-based gaming system 209 may select an order of alterations 309 within the chain based on various criteria. This order may be determined by: The severity of the unhealthy and/or potentially unhealthy conditions; The potential for alterations 309 to counteract one another; and also, or instead the type of alteration 309 the computer-based gaming system 209 determines is most appropriate.

In a multi-user scenario, whether local or online, the computer-based gaming system 209 may define a chain as at least one or more alterations 309 across at least one user 301 or more than one user 301. For example, if one user 301 is experiencing an unhealthy condition 307 and/or potentially unhealthy condition, and another user 301 is simultaneously experiencing an unhealthy condition 307 and/or potentially unhealthy condition, this may constitute an alteration 309 chain.

The computer-based gaming system 209 may resolve chains in different orders. One chain may resolve before another, or multiple chains may resolve simultaneously. The determination of resolution order may be based on different criteria such as: The severity of the unhealthy condition 307; The type of alterations 309 the computer-based gaming system 209 wants to make; and the potential impact on gameplay for each user 301.

The computer-based gaming system 209 may use machine learning and/or artificial intelligence to optimize the creation and/or resolution of alteration 309 chains, learning from past experiences to improve future responses.

After a chain link of alterations 309 is resolved, the computer-based gaming system 209 may implement a cooldown period before allowing further alterations 309. There may also be a predetermined maximum number, or select number of chain link alterations 309 the computer-based gaming system 209 may make.

The computer-based gaming system 209 may have a select maximum number of chain links and/or chain resolutions that may occur.

After each and/or all chain resolution(s), the computer-based gaming system 209 may implement a cooldown period to one or more but not all chain resolution(s) and/or all chain resolutions. During this cooldown period, one or more but not all alterations 309 may be prohibited, or all alterations 309 may be prohibited. After each chain link, the computer-based gaming system 209 may implement a cooldown period to one or more but not all chain link(s), during which no other chain link and/or alterations 309 may occur. The computer-based gaming system 209 may also implement a cooldown period after all chain links, during which no other chain links and/or alterations 309 may occur.

Here are some examples to illustrate how the chain of alterations 309 feature might work in practice:

Example 1: Single User Chain. A user 301 is playing an action game and the computer-based gaming system 209 detects elevated heart rate (Chain Link 1) and increased muscle tension (Chain Link 2)

Chain resolution: 1. The computer-based gaming system 209 first reduces game speed slightly (resolving Chain Link 2) 2. Then it lowers the brightness and contrast of the display (resolving Chain Link 1) The order is chosen to first address the immediate physical stress before adjusting visual elements.

Example 2: Multi-User Local Chain. Two users are playing a split-screen racing game. The first user shows signs of eye strain (Chain Link 1), while second user exhibits signs of stress (Chain Link 2).

Chain resolution: The computer-based gaming system 209 adjusts the color temperature for the first user's portion of the digital media display device 701 (resolving Chain Link 1) Then it reduces the intensity of vibration feedback for the second user's input peripheral 205 (resolving Chain Link 2).

Example 3: Online Multiplayer Chain. In an online multiplayer game, a user 301 shows signs of fatigue (Chain Link 1), another user 301 exhibits stress (Chain Link 2), and yet another user 301 has elevated blood pressure (Chain Link 3). Chain resolution: 1. The computer-based gaming system 209 increases break frequency for the first user 301 (resolving Chain Link 1) 2. It reduces in-game audio volume for the second user 301 (resolving Chain Link 2) 3. Finally, the computer-based gaming system decreases the game's difficulty for the third user 301 (resolving Chain Link 3).

Example 4: Counteracting Alterations 309 Chain. A user 301 playing a puzzle video game and is experiencing signs of both eye strain (Chain Link 1) and decreased cognitive performance (Chain Link 2). Chain resolution: 1. The computer-based gaming system 209 first increases the size of the digital media elements (resolving Chain Link 1) 2. Then it simplifies puzzle complexity (resolving Chain Link 2). This order may prevent the potential counteraction of alterations of making puzzles easier but harder to see.

Example 5: Severity-Based Chain. During a gaming session, a user 301 exhibits dehydration (Chain Link 1), severe eye strain (Chain Link 2), and moderate muscle tension (Chain Link 3). Chain resolution: 1. The computer-based gaming system 209 reduces screen brightness (resolving Chain Link 2) 2. It then may trigger a shoulder massage function in the gaming chair (resolving Chain Link 3) 3. Finally, it displays a hydration reminder (resolving Chain Link 1. The chain resolves based on the severity of the conditions, addressing the most severe first. This process/method may also be applied in local and multiplayer settings where there is more than one user 301 experiencing an unhealthy condition 307.

In some embodiments, the computer-based gaming system may include a "Chain of alterations" feature that manages how alterations are applied in response to unhealthy conditions. This feature may operate by monitoring for unhealthy conditions within a select time period and applying all necessary alterations at the end of that period.

For example, if a select time period of 30 seconds is defined, and multiple users experience unhealthy conditions within that time frame, the system may wait until the end of the 30-second period before applying the alterations. At that point, all alterations needed to address the unhealthy conditions are applied at once. The alterations may be applied in a pre-defined order or sequence, ensuring that all affected users receive the necessary adjustments in response to the detected conditions.

The computer-based gaming system 209 may also process simultaneous unhealthy condition 307 chain alterations 309. For example, consider a scenario in an online multiplayer game where more than one user 301 is experiencing different unhealthy conditions 307 simultaneously, and the computer-based gaming system 209 determines that these conditions are of equal severity and require immediate attention.

A user 301: Exhibiting signs of eye strain (Chain Link 1); Another user 301: Showing elevated heart rate (Chain Link 2); Yet another user 301: Displaying symptoms of hand fatigue (Chain Link 3). The computer-based gaming system 209 may decide to resolve this chain simultaneously. Simultaneous Chain Resolution: For the first user 301: The computer-based gaming system 209 adjusts screen contrast and color temperature (resolving Chain Link 1) For the second user 301: The computer-based gaming system 209 introduces periodic calm-down breaks in gameplay (resolving Chain Link 2) For the third user 301: The computer-based gaming system 209 reduces the required button press frequency (resolving Chain Link 3). All these alterations 309 may be implemented simultaneously.

The computer-based gaming system 209 may be capable of applying the same alteration 309 to one or more users who may be experiencing the same or different types of conditions. For example, Unified Alteration 309 for Multiple users. For example, a scenario in a multiplayer game where: a user 301: Is exhibiting signs of stress (elevated heart rate); Another user 301: Is showing symptoms of eye strain; Yet another User 301: Is displaying signs of stress.

The computer-based gaming system 209 may determine that a single type of alteration 309 could improve the unhealthy condition 307 and/or potentially unhealthy conditions for each of these users 301, regardless of their specific unhealthy conditions. The computer-based gaming system 209 implements a "calming mode" across the video game for each of these users 301.

This "calming mode" alteration 309 may involve: Softening the color palette of the game; Reducing the intensity of action sequences; Lowering the volume and tempo of background music; Introducing more frequent, short breaks in gameplay.

Application of the Unified Alteration 309: For User A and C: The calming mode may directly address their stress-related conditions by creating a more relaxing gaming environment. For User B: While not directly targeting eye strain, the softer color palette may provide some relief.

The computer-based gaming system 209 may apply this unified alteration 309 simultaneously to all users, regardless of their specific conditions.

The computer-based gaming system 209 may monitor the effectiveness of this unified alteration 309 on each of the users. If it detects that the alteration 309 is not sufficiently addressing a particular user's unhealthy condition(s), it may then implement additional, user-specific alterations 309.

After applying the unified alteration 309, the computer-based gaming system 209 may implement a cooldown period for all affected users. The duration of the cooldown period may be the same for all affected users or each user may have a different duration. The duration of the cooldown period may be the same for some affected users in the gaming session and different for other affected users in the gaming session. Users that were not affected by the unified alteration 309 may or may not be subject to the cooldown period also. If only one user 301 is experiencing an unhealthy condition 307, an alteration 309 may still be made where other users in the gaming session are affected by the cooldown period. During this period, the computer-based gaming system 209 may continue to monitor users vital sign information 305 and gather data on the effectiveness of the unified approach.

The computer-based gaming system 209 may apply a single, universal alteration 309 that addresses multiple different unhealthy condition 307 and/or potentially unhealthy conditions across various users. Here's an example of how this might work:

Example: One-Size-Fits-All Alteration 309 for Diverse unhealthy conditions. Consider a multiplayer gaming scenario where: User A: Exhibiting signs of eye strain User B: Showing symptoms of stress (elevated heart rate) User C: Displaying signs of hand fatigue User D: Experiencing decreased cognitive performance due to extended play. The computer-based gaming system 209 may determine that a single, alteration 309 could benefit all users, despite their diverse unhealthy conditions:

Universal Alteration 309: The computer-based gaming system 209 implements a "Rhythmic Gaming Mode" for all users.

This "Rhythmic Gaming Mode" may involve: Altering 309 the game's pace to follow a steady, calming rhythm; Adjusting visual elements to pulse gently in sync with this rhythm; Modifying control inputs to align with the rhythmic pattern; Introducing periodic, synchronized breaks in the gameplay flow.

Example of a Practical Application of the Universal Alteration 309: For User A (eye strain): The rhythmic visual pulsing may reduce eye strain by providing regular micro-breaks for the eyes. For User B (stress): The steady, predictable rhythm may help lower heart rate and reduce stress. For User C (hand fatigue): The rhythmic control inputs may provide regular moments of rest for the hands. For User D (cognitive fatigue).

The computer-based gaming system 209 may or may not apply this universal "Rhythmic Gaming Mode" simultaneously to all users. This approach may: Address multiple health concerns with a single, unified alteration 309.

The computer-based gaming system 209 may monitor each user's vital sign information 305 and digital media interaction information during the "Rhythmic Gaming Mode" to assess its effectiveness across different unhealthy conditions 307 and/or potentially unhealthy conditions. If the computer-based gaming system 209 detects that this universal alteration 309 is not sufficiently addressing a particular user's unhealthy condition 307, it may then consider implementing additional, user-specific alterations 309.

After applying the "Rhythmic Gaming Mode", the computer-based gaming system 209 may or may not implement a shared cooldown period for all affected users. During this period, it may continue to gather data on the effectiveness of this one-size-fits-all approach for future refinement.

Here's an example of how the computer-based gaming system 209 may apply a single, specific alteration 309 to address multiple different conditions: The computer-based gaming system 209 may apply a single alteration 309, such as adjusting screen brightness, to address multiple users experiencing different unhealthy or potentially unhealthy conditions.

Example: Universal Screen Brightness Adjustment. Consider a multiplayer gaming scenario where: User A: Exhibiting signs of eye strain User B: Showing symptoms of stress (elevated heart rate) User C: Displaying signs of mild headache The computer-based gaming system 209 may determine that a single alteration 309—adjusting screen brightness—could benefit all users, despite their diverse unhealthy conditions.

Practical Application of the Universal Alteration: For User A (eye strain): The reduced brightness may directly alleviate eye strain. For User B (stress): The dimmer screen may create a more calming visual environment, potentially helping to reduce stress. For User C (mild headache): The lower light output may reduce visual stimuli contributing to the headache.

The computer-based gaming system 209 may apply this universal brightness reduction simultaneously to all users 301. This approach may: Address multiple health concerns with a single alteration; Maintain a visual experience across one or more users; Simplify the alteration process in multiplayer scenarios.

The computer-based gaming system 209 may monitor each users vital sign information 305 and digital media 217 interaction data performance during this brightness alteration to assess its effectiveness across different conditions. If the computer-based gaming system 209 detects that this universal alteration is not sufficiently addressing a particular user's 301 unhealthy condition 307, it may then consider implementing additional, user-specific alterations.

After applying the brightness alteration, the computer-based gaming system 209 may implement a cooldown period for all affected users 301. The cooldown period may or may not be the same duration as other the other affected users and/or a different duration from other users. During this cooldown period, the computer-based gaming system may or may not continue to gather data on the effectiveness of this one-size-fits-all approach for future refinement.

This feature may allow the computer-based gaming system 209 to efficiently manage diverse health concerns in multiplayer scenarios, balancing individual needs with gameplay consistency while minimizing disruptions to the overall gaming experience.

A virtual reality headset or eyewear device such as smart glasses may be utilized by a user to improve or prevent an unhealthy condition or potential unhealthy condition that may result from the user's interaction with digital media. When worn, the eyewear device may alter the visual presentation of the digital media, with these alterations being perceptible only to the user interacting with the virtual reality headset.

An unhealthy condition 307 and/or a potentially unhealthy condition, along with saved alterations 309 and/or alteration packages 309, may be preloaded, transferred, downloaded, and/or assigned directly to an eyewear device. A user 301 of the eyewear device may also have the ability to set their own unhealthy condition 307 and/or potentially unhealthy condition on the device. Additionally, the user 301 may download and transfer alterations and/or alteration packages from the internet to the eyewear device. These alterations 309 can then be applied by the eyewear device to digital media in real-time, altering the digital media 217 in a way that is perceptible only through the eyewear device, thereby preventing or improving the unhealthy condition 307.

The virtual reality headset may be set to recognize the content a user 301 will interact with and/or identify digital media in real time. Based on the saved alterations 309 and alteration packages 309, the device may alter the digital media, such as a movie or video game, to prevent or improve an unhealthy condition 307.

Virtual reality headset may be configured to preload information about digital media content that the user 301 is likely to interact with, based on user preferences, history, or scheduled activities. For example, a user 301 may preload or assign a digital media movie onto the eyewear device. Using the user's 301 saved alterations, and/or alteration packages, and/or saved unhealthy conditions, and/or potentially unhealthy conditions, the eyewear device may prepare alterations 309 for the movie and/or apply these alterations 309 in real time as the user watches the movie, by utilizing any of the saved alterations, alteration packages, unhealthy conditions, and/or user preferences.

Example of how they virtual reality headset may work: Let's say a user 301 has and unhealthy condition 307 of hemophobia. The user 301 may set this unhealthy condition 307 onto the virtual reality headset, or the virtual reality headset may determine the user has hemophobia based on noticing changes in the user's 301 vital sign information 305 when scenes of blood appear. The user 301 selects a movie and the information of the movie is received by the virtual reality headset, where the content is analyzed. The virtual reality headset identifies scenes that may trigger the unhealthy condition 307 by utilizing the user's 301 stored information, such as the user's condition settings or vital signs or through real time analysis of the user's vital sign information 305 in conjunction with the digital media 217. The virtual reality headset then prepares to apply alterations in real-time. In this case, virtual reality headset, with a process, may alter the appearance of blood from the movie scenes either before the blood appears or as it appears in real time. These alterations 309 may be applied by the eyewear device to digital media 217 in real-time, altering the digital media 217 in a way that is perceptible only through the virtual reality headset, thereby preventing or improving the unhealthy condition 307. For another example, if a user 301 is an alcoholic or recovering alcoholic and this unhealthy condition 307 is set on the virtual reality headset, the user selects a movie, which is analyzed by the virtual reality headset. The device scans for scenes involving alcohol and prepares to alter them. When there is a scene involving actors interacting with alcohol, the virtual reality headset may change the alcohol to something more appropriate, such as milk or orange juice. Again, these alterations 309 may be applied in real-time, altering the digital media 217 in a way that is perceptible only through the virtual reality headset, thereby preventing or improving the unhealthy condition 307. This method/process may ensure that if theirs a shared digital media display device 701 amongst more than one user, each user can have a healthy experiencing enjoying the digital media 217. The virtual reality headset may also receive information and/or identify digital media 217 in real-time through visual recognition algorithms, content metadata, or wireless communication with media playback devices. The virtual reality headset may utilize a predetermined maximum number of alterations 309. For example, if the user 301 has an unhealthy condition 307 which is hemophobia and digital media 217 content the user is interacting with such as a video game or movie has 100 scenes with blood. The virtual reality headset may be configured to perform 100 maximum alterations 309 and no more after the 100 alterations 309 have been exhausted while the user 301 interacts with that specific digital media 217 content. If a user 301 were to switch to another form of digital media 217 content, such as another game or movie, regardless of it being during the same digital media 217 interaction session or a digital media 217 interaction session the next day, and this other digital media 217 content has 28 scenes with blood, then the predetermined maximum for that digital media 217 content is 28. If the user 301 were to rewatch and/or replay the digital media 217 content such as a video game and/or movie, the same number of alterations or more or less may regenerate, and/or the previously applied alterations may already be applied already for user 301. Less or more alterations being the predetermined maximum may occur when, previously made alterations are saved when a user re-interacts with the same digital media 217 content such as a video game and the previously made alterations are already applied to the digital media content but the user 301 may have developed another unhealthy condition 307 such as alcoholism and the digital media 217 content the user 301 is interacting with has 10 or 120 scenes that include alcohol. The predetermined maximum number of alterations may then be 10 or 120 which is more or less than the 28 alterations.

There may be a predetermined maximum for different scenes of a form of a digital media content such as a movie. For example, Blood scenes 28 maximum number of alterations 309, and alcohol scenes 120 maximum number of alterations. Cooldown period's may be applied after each alteration 309, and during this cooldown period, no further alterations 309 may occur. Cooldown period's may also be applied after all select maximum number of alterations 309 have been exhausted, and during this cooldown period, no further alterations 309 may occur.

A virtual reality headset may monitor a user's 301 vital sign's 303 in real time or utilize a preset unhealthy condition 307 of the user 301, such as epilepsy, and identify digital media content that may potentially trigger this condition. Upon identification, the system may alter the digital media by slowing it down, thereby reducing the likelihood of triggering the pre-set condition. This alteration may persist for the duration of the user's interaction with the digital media in the current session. For instance, as long as the user remains engaged with the digital media—such as watching a video, playing a game, or interacting with an application—the slowing alteration may be maintained.

In addition, the system may identify patterns within digital media, such as video games, to aid the user in completing tasks or challenges. This pattern recognition may facilitate alterations 309 in gameplay that favor the user, enhancing their ability to complete the game or overcome specific challenges while preventing and unhealthy condition 307 from being triggered or improving an unhealthy condition 307. Such adjustments may include slowing down certain in-game events or providing visual or auditorial cues to guide the user 301.

If the user 301 exits the digital media session, such as by removing the VR headset, getting up, or walking away, the system may recognize the cessation of interaction and subsequently terminate both the alteration and the pattern recognition aid. Upon termination, the system may initiate a cooldown period, during which further alterations 309 occur until after the cooldown period as elapsed.

In one embodiment, the computer-based gaming system may be configured to support multiple users interacting with digital media in various locations. The system is designed to monitor and respond to unhealthy conditions that may arise during the users'interactions with the media. By utilizing real-time vital sign monitoring or referencing pre-set unhealthy conditions, the system can make adjustments to ensure the health and well-being of the users.

For instance, one user of a computer-based gaming system may be interacting with digital media content at home, while another user of a virtual reality headset is interacting with digital media in a different location. The computer-based gaming system or VR headset may be connected to a host system, which processes vital sign information of the user(s) in real-time and/or references pre-set unhealthy conditions of the user(s). If an unhealthy condition is detected or the digital media triggers an unhealthy condition based on the user(s) preset unhealthy conditions, the one or more ways in which the user(s) interact with the digital media may be altered in a manner to improve the unhealthy condition(s) of the user(s) and/or prevent a preset unhealthy condition of the user(s) from being triggered.

In some embodiments, the computer-based gaming system may include a learning and analysis component that prevents premature or unnecessary alterations to the user's interaction with digital media. This may allow the system to monitor patterns in vital signs/biometric information over time, determining whether an unhealthy condition is truly caused by the media content. This approach may ensure that alterations are applied only when a genuine link between the media and the unhealthy condition is established.

For example, the system detects a rise in the user's heart rate while a clown appears on the screen, it may not immediately trigger any alteration in response to this rise of the user's heart rate, as the increase may not be caused by the clown. The system may continue to monitor the user's vital signs and may observe that the heart rate remains above the user's regular threshold. However, no alteration may be made at this stage.

If the clown appears again and the heart rate rises further beyond the regular or current threshold, the system may still refrain from altering the media to gather additional information. Alternatively, the system may determine that the clown is likely contributing to the unhealthy condition, based on the repeated rise in heart rate above the threshold whenever the clown appears and alter the clown in a manner to improve the unhealthy condition.

In addition, at least one singular type of alteration, may occur (e.g., turning the clown into, a teddy bear) in response to the unhealthy condition of a user. This alteration may occur instantly due to graphics being rendered in real time. Another alteration may not occur until another unhealthy condition is triggered by the one or more ways in which the user interacts with the digital media, and/or if a preset unhealthy condition may be triggered by the one or more ways in which the user interacts with the digital media.

In scenarios where the alteration is not instant, the system may continue the alteration process for a period of time. During this time, a new alteration may or may not be added to the current alteration. Once the one or more ongoing alteration concludes either because the user's vital signs improve or based on a select time period, no further alterations may occur until another unhealthy condition is triggered by the one or more ways in which the user interacts with the digital media, and/or if a preset unhealthy condition may be triggered by the one or more ways in which the user interacts with the digital media.

An alteration that may occur instantly, such as transforming a clown to a teddy bear, may be considered completed upon the system successfully altering the clown into the teddy bear. For an alteration that is not instant, such as an ongoing alteration, the alteration may be considered completed once the user's vital sign information improves or until the duration of the alteration has ended.

In some embodiments, the system may include a vital sign detector that is required to remain attached to the user throughout the duration of gameplay. This ensures that any physiological data collected, such as heart rate or respiration rate, accurately reflects the user's current state while interacting with the digital media. The system is designed to prevent manipulation by ensuring that the vital sign detector remains continuously attached during gameplay.

For example, if a user were to remove the vital sign detector to get a package, they may engage in physical activity such as running up and down stairs to quickly finish the task and get back to the video game. However, this may raise their heart rate in a way that was likely not caused by the digital media. When the user reattaches the vital sign detector upon returning to the game, the system may recognize this heart rate increase and could alter the digital media in response. To avoid this, the system may be programmed to detect when the vital sign detector is removed or reattached, or if it is no longer receiving vital sign information from the user.

The system may respond by checking the user's vital signs, such as heart rate, at the time the detector was removed. When the user puts the device back on, the system compares the vital sign information from before the detector was removed with the user's current vital sign information, such as heart rate. If the user's current heart rate is above what it was when the user removed the vital sign detector, the system may refrain from causing any alterations in response to this increase. Once the user's vital signs return to what they were before the vital sign detector was removed, and during digital media interaction the heart rate increases, the system may then alter one or more ways in which the user interacts with the digital media in a manner to improve the unhealthy condition.

Additionally, the system may include a camera or motion sensors to monitor whether the user remains seated or physically present during gameplay. The camera may confirm whether the user is engaged with the game or has left the gaming setup to perform activities outside of the game that could artificially alter their vital signs. For example, if the camera detects that the user has left the seated position and is performing activities like running up and down stairs, the system may suspend any alterations to the digital media until the user returns to their seated position and the vital sign detector is securely reattached.

In an alternative embodiment, the system may combine data from the vital sign detector and the camera to ensure that gameplay alterations are not applied when the vital sign fluctuations are caused by external activities. If discrepancies are identified (e.g., the user's heart rate increased after performing physical activity rather than due to the game), the system may prevent or delay alterations until the vital signs stabilize.

The system may also or instead include a user-initiated control that allows the user to notify the system when their vital signs may fluctuate due to external factors unrelated to the game. For instance, if a user knows that their heart rate will increase for reasons not related to the game, they can provide input to the system to avoid alterations in response to these fluctuations. The system may also generate logs or reports that track when the vital sign detector is removed or reattached, ensuring transparency in gameplay monitoring.

The word likely when used herein means more likely than not based on current medical information.

In some embodiments, the system may include a "Select maximum" functionality that controls how alterations in response to unhealthy condition(s) of a user are applied when a user replays or starts a new game. This functionality ensures that alterations are either retained or reset depending on the user's interaction with the game, offering flexibility while managing unhealthy conditions.

When a game ends, if the user chooses to replay and loads into the previously completed saved state (e.g., the storyline or other progression data), no new alterations may be applied to the saved data. This allows the user to experience the completed game as it was altered during the initial playthrough, without introducing additional changes.

If the user starts a new game and does not load the previously saved state, two possible scenarios may occur. First, all alterations from the completed or progressed game may be carried over and applied to the new game. Second, the system may reset the selected or predetermined maximum limit of alterations, allowing new alterations to be applied in response to unhealthy conditions during the new playthrough.

By incorporating this functionality, the system can manage how alterations are applied across multiple playthroughs, ensuring that users either retain prior alterations or start fresh with a reset limit, depending on their preferences or health needs.

In some embodiments, the system may alter the progression of a game based on the user's physiological response to certain scenes. For example, during a cutscene featuring a dragon that makes a scary face, if the user's heart rate increases, the system may trigger a specific scene programmed to play in response to this event. This scene may be designed to address or mitigate the unhealthy condition caused by the heart rate rise.

If no heart rate rise or unhealthy condition is detected, the game will continue as planned, playing the next scene that is programmed to follow in the absence of an unhealthy condition.

Figure 10:
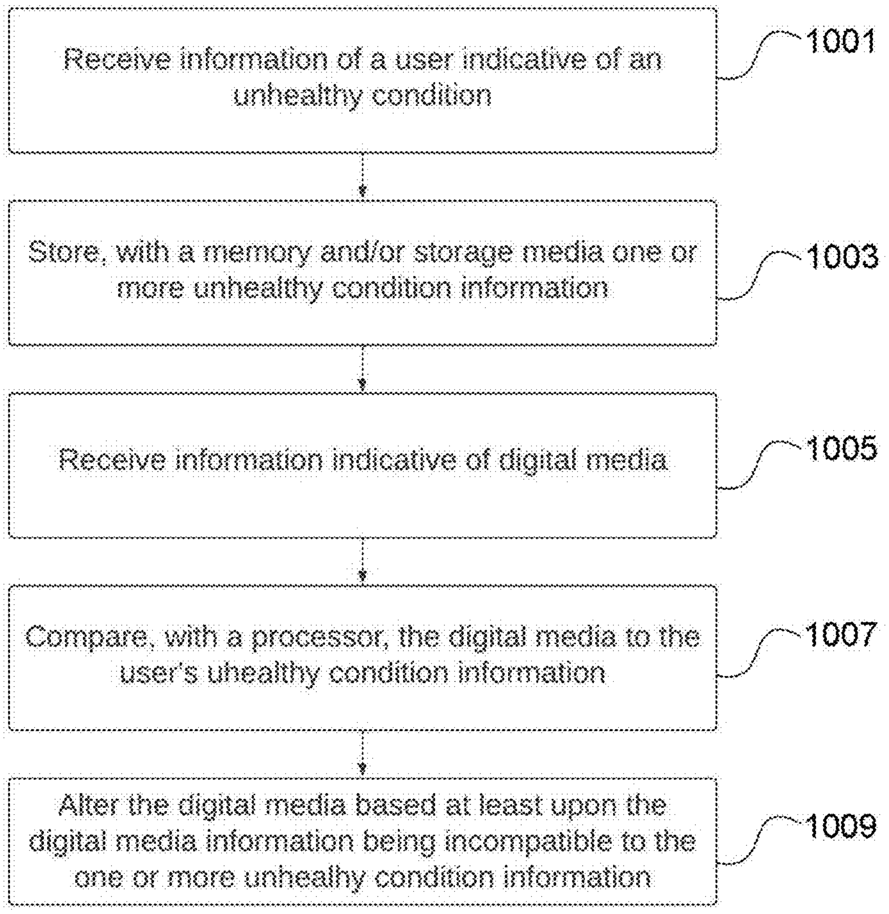
FIG. 10 illustrates an example of a process of a computer-based gaming system that alters one or more ways in which a user interacts with digital media in response to an unhealthy condition.

FIG. 10 illustrates a process 1000 that is used for a computer-based gaming system 209. At block 1001, the system receives information indicative of a user's 301 unhealthy condition. This information may be obtained through various means, including but not limited to user input, pre-set conditions configured by the user, or data gathered from sensors and/or other vital sign and/or biometric monitoring devices. For instance, a user may set a condition to avoid viewing certain types of content, such as alcohol-related imagery, due to a history of alcoholism. The system may not require an exact phrase to be entered when defining this preset condition. Instead, users may enter text that generally describes scenarios or content that could trigger an unhealthy condition. For example, rather than entering the specific phrase "alcoholism," the user could input a description of triggers related to alcohol consumption or environments associated with alcohol use. The system can interpret these inputs and adjust the user's interaction with digital media accordingly, helping to prevent triggering the unhealthy condition.

Next, at block 1003, the system may store the unhealthy condition information within its memory and/or storage media. This storage may allow the system to reference the unhealthy condition information as the user interacts with digital media and/or before the user interacts with digital media. The storage may occur in a variety of formats, including but not limited to databases, flat files, or structured storage mechanisms within the system's architecture.

At block 1005, the system receives information indicative of digital media that the user may interact with or is interacting with. This may include content being displayed on a digital media display device, such as a TV, computer screen, or an AR headset, VR headset, or an MR headset. The information received may involve metadata associated with the digital media, content tags, or real-time analysis of the media's visual or auditory components. Additionally, the system may be configured with components such as CD drives, ROM slots, USB ports, or other media input interfaces to receive physical media containing digital content. Upon receiving such physical media, the system may preload and/or analyze the contents to determine if they include any elements that might conflict with the user's unhealthy condition information. This may allow the system to prepare in advance and ensure that any potential triggers within the digital media are addressed before the user interacts with the content. Furthermore, the system may also work in conjunction with external devices capable of receiving physical media, such as DVD players, Blu-ray players, or other media drives. When connected, the system can access and analyze the content from these devices either before the user begins interacting with it and/or in real-time. The user may select digital media, such as a movie, video game, music, that may be from a library of available content. They may do this through internet access by the computer-based gaming system. Once selected, the system can preload the media and analyze its contents before the user begins interacting with it, allowing the system to detect and address any elements that may conflict with the user's predefined unhealthy condition information. Alternatively, or in addition, the system may analyze the media in real-time as the user interacts with it, continuously monitoring for and altering any content that might trigger an unhealthy condition. Additionally, the system may be configured to utilize a predetermined maximum number of alterations during the interaction with digital media content. For example, if the user has an unhealthy condition, such as hemophobia, and the digital media content the user is interacting with includes 100 scenes with blood, the digital media alteration system may be configured to perform a maximum of 100 alterations.

In block 1007, the system compares, the received digital media information to the user's unhealthy condition information using the processor. This comparison involves analyzing whether the content of the digital media aligns with or conflicts with the pre-defined unhealthy conditions stored in the system. For example, if the digital media contains incompatible information such as imagery of a bottle of whiskey to the user's health condition(s) such as alcoholism that may trigger an unhealthy condition such as the user relapsing, the system recognizes this conflict based on the comparison.

Finally, at block 1009, the system alters the digital media based at least upon the digital media information being incompatible with the one or more unhealthy condition information. This alteration may involve altering the visual or auditory representation of the digital media that is perceptible and/or audible to the user. For example, the system may replace an image of a whiskey bottle with a non-alcoholic alternative, such as a milk carton, thereby preventing an unhealthy condition from being triggered. Additionally, the system may detect the user's heart rate increasing during scene(s) containing blood and remove the blood in real-time to maintain the user's comfort and prevent triggering an unhealthy condition. The system may then save this information and may suggest the user has hemophobia.

Figure 11:
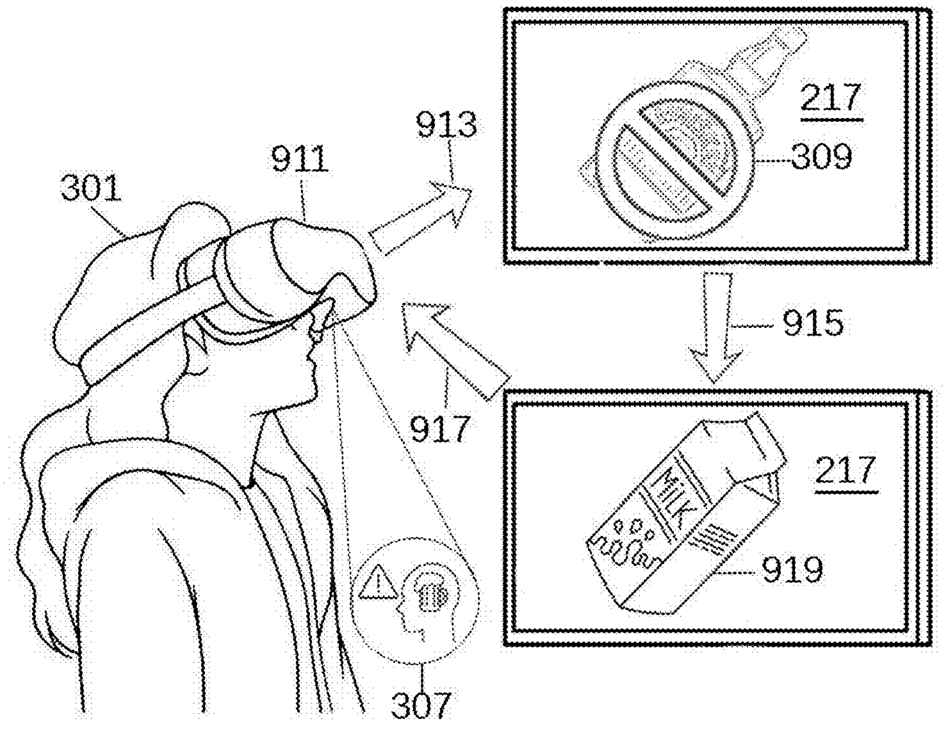
FIG. 11 is an example of a computer based-gaming system altering functionalities in the digital media in response to a user's predefined unhealthy condition.

FIG. 11 illustrates a scenario where a user 301 is interacting with a computer-based gaming system eyewear apparatus 911 that uses the process 1000 illustrated in FIG. 10. The process illustrated in FIG. 10 is not limited to eyewear apparatus. The process may be used in a computer-based gaming system, a television system etc. The computer-based gaming eyewear apparatus 911 may be any form of eyewear technology, including but not limited to, smart glasses, augmented reality (AR) headsets, virtual reality (VR) headsets or mixed reality (MR) headsets. The digital media the user 301 is interacting with originally contains a scene that shows a whiskey bottle, which is recognized by the eyewear device 911 as incompatible with the user's unhealthy condition and may trigger of an unhealthy condition in the user. For illustrative purposes, the unhealthy condition 307 is visually represented by an icon showing a beer and an exclamation mark, indicative of a condition such as alcoholism. This unhealthy condition 307 was pre-set and stored by the user operating the eyewear apparatus 911 process blocks 1001 and 1003 (FIG. 11).

As the user 301 views the digital media 217 through the eyewear device 911, the process 1000 block 1005 (FIG. 11) identifies by a processor the whiskey bottle in the original digital media scene as being incompatible with the user's unhealthy condition and may trigger the unhealthy condition 307 in the user process 1000 block 1007 (FIG. 11). This recognition is illustrated by the arrow labeled 913, which points from the user 301 wearing the eyewear apparatus 911, to the whiskey bottle in the digital media 217.

Upon recognizing the incompatible digital media that may trigger an unhealthy condition, the eyewear apparatus 911 alters how the user 301 perceives the digital media 217 in a manner to prevent the unhealthy condition from being triggered by changing the whiskey bottle to compatible digital media 919 which is a milk carton in this example process 1000 block 1009 (FIG. 11). This alteration process is represented by the arrow labeled 915, which points towards the milk carton as the result of the alteration and as the new perception of the whiskey bottle.

Finally, the user 301 perceives the altered digital media where the whiskey bottle has been altered to compatible digital media 919 which is then a milk carton, as indicated by the arrow labeled 917. The alteration may only be perceptible through the eyewear apparatus 911 the user 301 is operating. This may mean the actual digital media 217 that may be displayed on a digital media display device 701 remains unaltered.

FIG. 12 illustrates a flowchart that represents the process by which a computer-based gaming system identifies and responds to unhealthy conditions of a user. The process begins at step 3001, where the system starts the session and begins monitoring the user 301.

At step 3005, the system receives vital sign information of the user. This may include, but is not limited to, heart rate, sweat levels, body temperature, and other physiological indicators that the system can gather through various input peripherals, such as wearable sensors or handheld devices. The computer-based gaming system 209 continuously receives and monitors this information throughout the digital media interaction session.

Simultaneously, at step 3003, the system receives facial information of the user. This facial information may include visual data gathered through a webcam or similar device, such as facial expressions, skin tone changes, or eye-tracking information 306. The eye-tracking information 306, for example, may allow the computer-based gaming system 209 to determine where the user 301 is focusing their gaze during the interaction, which may be a factor in assessing alterations 309.

At decision point 3007, the computer-based gaming system 209 analyzes the received information to determine whether the user 301 is exhibiting an unhealthy condition 307. This analysis involves comparing the vital sign and/or physiological and/or biometric information (received at step 3005) and the facial and/or eye-tracking information 306 (received at step 3003) to predefined thresholds that represent an unhealthy condition 307, such as elevated heart rate, excessive sweating, and/or gaze on stressful digital media elements that may be the cause of stress. If the computer-based gaming system 209 determines that the user 301 is not experiencing an unhealthy condition 307, the process loops back to steps 3003 and 3005 for continued receiving and monitoring of the user's 301 information.

If the computer-based system 209 identifies that the user 301 is experiencing an unhealthy condition 307 that may be caused by one or more ways in which the user 301 interacts with the digital media 217, it proceeds to step 3009. At this step, the computer-based gaming system 209, with a processor, triggers an alteration 309 based on the received information in response to the unhealthy condition 307 in a manner to improve the user's 301 unhealthy condition 307 while the user 301 continues to interact with the digital media 217.

After the alteration has been triggered, the computer-based gaming system returns 209 to steps 3003 and 3005 to continue monitoring the user's physiological and facial information, ensuring that the alteration effectively mitigates the unhealthy condition. Also, the computer-based gaming system 209 may apply a cooldown period, during which, no further alterations 309 are made by the computer-based gaming system 209 even if an unhealthy condition 307 is detected.

FIG. 13 illustrates a digital media interaction session consisting of a war simulation video game where the digital media 217 the user 301 is interacting with is being displayed by a digital media display device 701. A webcam 236 that may gather facial information of the user 301 and/or eye-tracking data 306. The eye tracking data 306 which is depicted by dotted lines from the user 301 during gameplay, is being received by the computer-based gaming system 209 represented by the downward aiming arrow. The user 301 is also depicted holding an input peripheral 205, which detects sweat levels 303 and heart rate information 303 which is being received by the computer-based gaming system 209 as the user 301 interacts with the digital media 217. The digital media 217 displays a digital depiction of the input peripheral 205 the user 301 is currently interacting with, circled in dotted lines, which represent the user's eye-tracking data 306 gazing at the digital depiction of the input peripheral 205. The computer-based gaming system 209 identifies an unhealthy condition 307 by receiving information indicative of excessive sweating and abnormal heart beat information 305. The computer-based gaming system 209 may analyze this vital sign/biometric information 305 in combination with eye-tracking information 306 to determine if the user's unhealthy condition 307 is caused by one or more ways in which the user is interacting with the digital media and trigger an alteration 309. As illustrated, the elevated sweat level information 305 and the elevated heartbeat information 305, together with the eye-tracking information 306, triggers the computer-based gaming system 209 to initiate an alteration 309 based on this received eye tracking information 306 and vital sign/biometric information 305. This alteration 309 as illustrated shows the eye tracking data 306 circling a digital depiction of the input peripheral 205, and based on this eye tracking information 306 and the vital sign/biometric information 305, alters 309 the physical input peripheral the user 301 is interacting with in a manner to improve the unhealthy condition 307 such as activating a cooling mechanism in the input peripheral 205.

FIG. 14 illustrates a flowchart of a process for managing and applying alterations in response to the detection of an unhealthy condition during a digital media interaction session.

At step 4001, the computer-based gaming system receives vital sign information from one or more users. This information may include heart rate, heartbeat, blood pressure, muscle tension, eye movement, and other biometric and/or vital sign information to asses a user(s) health status during digital media interaction. The system continuously monitors these vital signs to detect any signs of unhealthy or potentially unhealthy conditions.

At decision block 4003, the system analyzes the received vital sign information to determine whether any user is experiencing an unhealthy condition or potentially unhealthy condition within a predetermined time period. If no unhealthy condition is detected, the process returns to step 4001, where the system continues to monitor and receive vital sign information from the users. If an unhealthy condition is detected, the process proceeds to step 4005.

At step 4005, upon detecting one or more unhealthy conditions, the system creates a chain of alterations corresponding to the detected conditions. A chain is formed when multiple unhealthy conditions are detected or multiple alterations to improve an unhealthy condition are required, within a select time period, either in a single user or across multiple users. Each alteration in the chain is designed to address a specific unhealthy condition to improve the user's health.

At decision block 4007, the system selects the order in which to apply the alterations within the chain. The order may be determined based on various criteria, including the severity of conditions, potential counteractions between alterations, the type of alterations, and the impact on the digital media interaction. The system may select from the following orders: Last-In-First-Out (LIFO) at step 4009, where the most recently detected unhealthy condition or alteration is addressed first; First-In-First-Out (FIFO) at step 4011, where unhealthy conditions of one or more user's or alterations are addressed in the order they were detected or triggered; or a custom order at step 4013, determined by the system based on the factors mentioned above.

At step 4015, the system applies, with a processor, the alterations based on the selected order to improve the unhealthy conditions of one or more user's involved in the chain link resolution.

Figure 15:
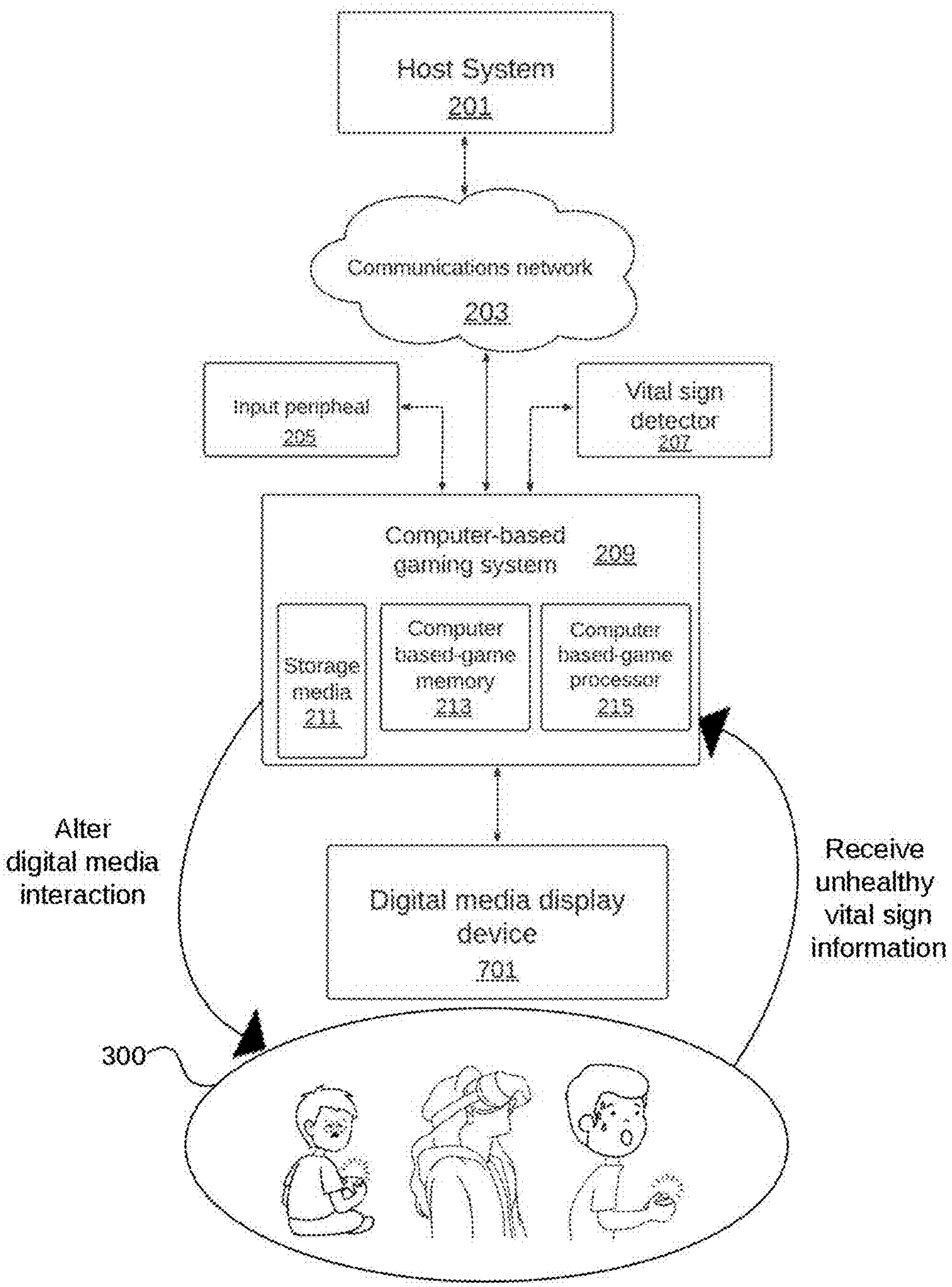
FIG. 15 illustrates a flow chart of an example of a process of a computer-based gaming system.

FIG. 15 illustrates the interaction between multiple users 300 and the FIG. 2 architecture for a computer-based gaming system 209. The users 300 are shown within an enclosed area, indicating their interaction with the one or more computer-based gaming systems 209 that generate digital media the user(s) 300 may interact with. This figure represents scenarios where there may be one or more users interacting either locally or through an online networked environment.

The arrow labeled "Unhealthy vital sign information" represents the flow of vital sign and/or biometric information from the users 300 to the computer-based gaming system 209 that is indicative of an unhealthy condition 307. The system receives vital sign and/or biometric information from multiple users using various input methods, such as wearable devices, sensors, or peripherals. This information is processed by the computer-based gaming system 209, which may include components like storage media 211, computer-based game memory 213, and a computer-based game processor 215. These components work collaboratively to analyze the data and identify if alterations to the digital media interaction are necessary to improve or prevent the users'unhealthy conditions. The arrow labeled "Alter digital media interaction" illustrates how one or more ways in which user(s) may interact with the digital media are altered in a manner to improve the unhealthy condition(s). The computer-based gaming system may perform any of the processes described in FIG. 1, FIG. 3, FIG. 4, FIG. 5, FIG. 6, FIG. 7, FIG. 9, FIG. 10, FIG. 11, FIG. 12, FIG. 13, and FIG. 14.

While this figure shows a single computer-based gaming system 209 connected to a host system 201 through a communications network 203, this setup may represent one of multiple possible configurations. In some embodiments, each user 300 may interact with their own individual computer-based gaming system 209, with each system potentially connected through the communications network 203 and host system 201. This flexibility may accommodate both local play, where users 300 may share the same gaming system, and online play, where users 300 may operate separate systems. The network architecture may ensure that vital sign and/or biometric information and/or alteration responses can be managed either within a single computer-based gaming system 209 or across multiple computer-based gaming systems 209.

The system may store all vital sign information and gameplay data (such as health metrics and alterations) on a blockchain ledger. Each change, whether it is an alteration applied in response to a detected unhealthy condition or an update to vital sign data, may be recorded as a block on the blockchain, making the entire history verifiable by both the system and the users.

The system may also use smart contracts on the blockchain to manage and trigger alterations in response to unhealthy conditions. In some embodiments, the system may feature a decentralized marketplace where users can download or purchase alteration packages that modify their gaming experience in response to their health data. Each alteration package could be represented as a non-fungible token (NFT) on the blockchain, allowing users to verify ownership and securely transfer these digital assets.

In multiplayer settings, blockchain technology may be used to manage health-related alterations across multiple players. The system can store vital sign data and game state information on a distributed ledger to ensure fairness and transparency in gameplay alterations.

The system may also reward a user for improving their health metrics during gameplay by issuing blockchain-based tokens. For example, if a user's vital signs are improved by an alteration implemented by a computer-based gaming system in response to an unhealthy condition of a user that is caused or is likely caused by one or more ways in which the user is interacting with the digital media, the system may award cryptocurrency or tokens stored on the blockchain that may be used for in-game rewards or other benefits.

In certain embodiments, after making an alteration in response to detecting an unhealthy condition of a user, the system may wait for a period longer than the cumulative time required for sensor data acquisition and processing before making any further alterations to the user's interaction with the digital media. This wait helps ensure that the system does not make successive adjustments too quickly. During this waiting period, the system may continue to monitor the user's vital signs but will not initiate further alterations until another unhealthy condition is detected after the wait.

For example, if the system typically takes 3 seconds to acquire and process sensor data, the wait period may be at least 4 or more seconds. During this wait, the system continues to monitor the user's vital signs but refrains from making additional alterations, even if another unhealthy condition is detected.

In some embodiments, information involving processes, methods, unhealthy conditions, and alterations—whether described herein or occurring during use of the computer-based gaming system—may be transmitted to an AI or machine learning component. This AI component may analyze the data to enhance its capability to detect unhealthy conditions and recommend or apply appropriate alterations in future interactions with the system.

It's imperative to recognize that the scenarios outlined are illustrative and by no means comprehensive. The realm of digital interaction is vast, and the consequences of changes within this sphere can vary widely based on the specific context and user needs.

Components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

Except as otherwise stated immediately above, nothing that has been stated or illustrated is intended or should be interpreted to cause a dedication of any component, step, feature, object, benefit, advantage, or equivalent to the public, regardless of whether it is recited in the claims.

The terms and expressions used herein have the ordinary meaning accorded to such terms and expressions in their respective areas, except where specific meanings have been set forth. Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by "a" or "an" does not, without further constraints, preclude the existence of additional elements of the identical type.

The invention claimed is:

1. Non-transitory computer-readable storage media containing a program of instructions that, when run in conjunction with a computing system that generates digital media that a user of the computing system can interact with in one or more ways:

receives information indicative of at least one vital sign of the user;

determines whether the received information is indicative of an unhealthy condition in the user that may be caused by one or more of the ways in which the user interacts with the digital media; and in response to a determination that the received information is indicative of such an unhealthy condition in the user: alters one or more but not all of the ways in which the user may interact with the digital media that is or are contributing to the unhealthy condition in the user in a manner that improves the unhealthy condition while the user continues to interact with the digital media; and after making such alterations in response to the determination of the unhealthy condition, does not make any further alterations to the one or more ways in which the user may interact with the digital media in response to an unhealthy condition while the user continues to interact with the digital media until after a set cooldown period.

2. The non-transitory computer-readable storage media of claim 1 wherein:

the received information indicative of at least one vital sign of the user includes information indicative of the user's respiratory rate; and the unhealthy condition that the system determines the received information is indicative of includes an unhealthy respiratory rate.

3. The non-transitory computer-readable storage media of claim 1 wherein:

the received information indicative of at least one vital sign of the user includes information indicative of the user's blood pressure; and the unhealthy condition that the system determines the received information is indicative of includes an unhealthy blood pressure.

4. The non-transitory computer-readable storage media of claim 1 wherein:

the received information indicative of at least one vital sign of the user includes information indicative of the user's temperature; and the unhealthy condition that the system determines the received information is indicative of includes an unhealthy temperature.

5. The non-transitory computer-readable storage media of claim 1 wherein:

the received information indicative of at least one vital sign of the user includes information indicative of the user's EEG readings; and the unhealthy condition that the system determines the received information is indicative of includes an unhealthy EEG reading.

6. The non-transitory computer-readable storage media of claim 1 wherein:

the at least one vital sign of the user includes the rate of the user's heartbeat; and the determination of whether the received information is indicative of an unhealthy condition in the user is based on the rate of the user's heartbeat.

7. The non-transitory computer-readable storage media of claim 1 wherein the program of instructions utilizes artificial intelligence to help determine which of the one or more ways in which the user may interact with the digital media should be altered to help improve the unhealthy condition.

8. The non-transitory computer-readable storage media of claim 7 wherein the artificial intelligence analyzes a history of the user's vital sign and the way in which the user was interacting with the digital media at each point in this history to help determine which of the one or more ways in which the user may interact with the digital media should be altered to improve the unhealthy condition.

9. The non-transitory computer-readable storage medium of claim 1, wherein the determination of whether the received information is indicative of the unhealthy condition is based on whether a change in the at least one vital sign satisfies a user-defined sensitivity level.

10. The non-transitory computer-readable storage media of claim 1 wherein the digital media is presented using web-browsing functionality of the computing system.

11. The non-transitory computer-readable storage media of claim 1 wherein vital sign information is displayed to the user while the user interacts with the digital media.

12. The non-transitory computer-readable storage media of claim 11 wherein the vital sign information is displayed as at least one of a numerical value, a graph, or a color-coded indicator.

13. The non-transitory computer-readable storage media of claim 11 wherein display of the vital sign information may be toggled on or off by the user.

14. The non-transitory computer-readable storage media of claim 1 wherein the computing system maintains a log of alterations applied during a digital media interaction session.

15. The non-transitory computer-readable storage media of claim 14 wherein the log is accessible to the user.

16. The non-transitory computer-readable storage media of claim 14 wherein the log is accessible to one or more persons monitoring the user's digital media interaction session.

17. The non-transitory computer-readable storage media of claim 14 wherein the computing system analyzes the log to identify patterns in the user's health over time.

18. The non-transitory computer-readable storage media of claim 14 wherein data from the log informs future alteration decisions.

19. The non-transitory computer-readable storage media of claim 14 wherein the computing system generates personalized health recommendations based on the log.

20. Non-transitory computer-readable storage media containing a program of instructions that, when run in conjunction with a computing system that generates digital media that a user of the computing system can interact with in one or more ways:

receives information indicative of at least one vital sign of the user;

determines whether the received information is indicative of an unhealthy condition in the user that may be caused by one or more of the ways in which the user interacts with the digital media; and in response to a determination that the received information is indicative of such an unhealthy condition in the user: alters one or more but not all of the ways in which the user may interact with the digital media that is or are contributing to the unhealthy condition in the user in a manner that improves the unhealthy condition while the user continues to interact with the digital media and limits the number of times the digital media interaction is altered for the user in response to an unhealthy condition caused by one or more ways in which the user interacts with the digital media to a predetermined maximum number of alterations.

* * * * *